US011642320B2

(12) United States Patent
Fattal et al.

(10) Patent No.: US 11,642,320 B2
(45) Date of Patent: May 9, 2023

(54) NANOPARTICULATE PRODRUGS

(71) Applicants: CENTRE NATIONAL DE LA RECHERCHE SCIENTIFIQUE, Paris (FR); UNIVERSITÉ PARIS-SUD 11, Orsay (FR)

(72) Inventors: Elias Fattal, Paris (FR); Nicolas Tsapis, Paris (FR); Mathilde Lorscheider, Saint-Louis (FR); Romain Canioni, Versailles (FR); Franceline Reynaud, Navegantes (BR)

(73) Assignees: CENTRE NATIONAL DE LA RECHERCHE SCIENTIFIQUE, Paris (FR); UNIVERSITE PARIS-SACLAY, Gif sur Yvette (FR)

( * ) Notice: Subject to any disclaimer, the term of this patent is extended or adjusted under 35 U.S.C. 154(b) by 519 days.

(21) Appl. No.: 16/334,598

(22) PCT Filed: Sep. 20, 2017

(86) PCT No.: PCT/EP2017/073740
§ 371 (c)(1),
(2) Date: Mar. 19, 2019

(87) PCT Pub. No.: WO2018/054953
PCT Pub. Date: Mar. 29, 2018

(65) Prior Publication Data
US 2021/0275462 A1  Sep. 9, 2021

(30) Foreign Application Priority Data
Sep. 20, 2016 (EP) ..................... 16189635

(51) Int. Cl.
*A61K 9/51* (2006.01)
*A61K 31/573* (2006.01)
(52) U.S. Cl.
CPC .......... *A61K 9/5153* (2013.01); *A61K 9/5138* (2013.01); *A61K 9/5192* (2013.01); *A61K 31/573* (2013.01)
(58) Field of Classification Search
CPC .. A61K 9/5153; A61K 9/5138; A61K 9/5192; A61K 31/573; A61K 9/5146
See application file for complete search history.

(56) References Cited

U.S. PATENT DOCUMENTS

| 2004/0018242 A1* | 1/2004 | Cunningham | A61K 9/145 424/489 |
| 2006/0216353 A1* | 9/2006 | Liversidge | A61K 9/008 424/489 |
| 2014/0079642 A1* | 3/2014 | Benita | A61K 38/13 424/9.6 |
| 2014/0329913 A1* | 11/2014 | Hanes | A61K 9/0036 514/772.1 |
| 2015/0337006 A1 | 11/2015 | Barman et al. | |

FOREIGN PATENT DOCUMENTS

| JP | 2007001926 A | 1/2007 |
| WO | 2014/160956 A2 | 10/2014 |

OTHER PUBLICATIONS

Cruje et al, Polyethylene glycol density and length affects nanoparticle uptake by cancer cells, MedCrave, vol. 1, Issue 1. (Year: 2014).*
Brand et al., "Collagen-induced arthritis," Nature Protocols, vol. 2, No. 5, 2007, pp. 1269-1275.
Gomez-Gaete et al., "Encapsulation of dexamethasone into biodegradable polymeric nanoparticles," International Journal of Pharmaceutics, 331 (2007), pp. 153-159.
Peracchia et al., "Stealth PEGylated polycyanoacrylate nanoparticles for intravenous adminstration and splenic targeting," Journal of Controlled Release 60 (1999) pp. 121-128.
Stewart, John Charles Marshall, "Colorimetric Determination of Phospholipids with Ammonium Ferrothiocyanate," Analytical Biochemistry 104, 10-14 (1980).
Surace et al., "Lipoplexes Targeting the CD44 Hyaluranic Acid Receptor for Efficient Transfection of Breast Cancer Cells," Molecular Pharmaceutics, vol. 6, No. 4, pp. 1062-1073, 2009.
International Search Report, dated Nov. 21, 2017, from corresponding PCT/EP2017/073740 application.
EP Search Report, dated Feb. 21, 2017, from corresponding EP 16 18 9635 application.

* cited by examiner

*Primary Examiner* — Mina Haghighatian
(74) *Attorney, Agent, or Firm* — Nixon & Vanderhye

(57) ABSTRACT

The present invention relates to anti-inflammatory drug formulation. Especially, this invention relates to corticosteroid prodrug nanoparticle. In a first aspect, this invention relates to a nanoparticle comprising a therapeutic agent and a surface coating material. The invention also relates to a process of manufacturing at least one nanoparticle of invention. The invention also relates to pharmaceutical composition and pharmaceutical kits.

14 Claims, 11 Drawing Sheets

NANOPARTICULATE PRODRUGS

FIELD OF INVENTION

The present invention relates to anti-inflammatory drugs formulation. Especially, this invention relates to glucocorticoid prodrug nanoparticles. In a first aspect, this invention relates to a nanoparticle comprising a glucocorticoid prodrug and a surface coating material. The invention also relates to a process of manufacturing at least one nanoparticle of invention. The invention also relates to pharmaceutical compositions and kits thereof.

BACKGROUND OF INVENTION

Glucocorticoids have demonstrated to be efficient anti-inflammatory drugs for the treatment of acute and chronic inflammatory diseases or autoimmune diseases. Despite this recognized therapeutic efficacy, the use of glucocorticoids in the treatment of inflammatory autoimmune type diseases is currently controversial. Indeed, glucocorticoids exhibit unfavorable pharmacokinetics characterized by poor tissue distribution and rapid elimination from the blood. As the pharmacokinetic profile is unfavorable for obtaining high concentrations of glucocorticoids to inflammatory sites, their systemic administration requires chronic use of high doses, resulting in several side effects.

Therefore, the development of a glucocorticoid drug formulation for systemic administration, favorable for obtaining high concentrations of glucocorticoids to inflammatory sites, and resulting in reduced side effects is highly needed.

The incorporation of glucocorticoid drugs into nano/microparticulate delivery systems represents a therapeutic opportunity. Gomez-Gaete et al., disclose the encapsulation of dexamethasone into PLGA nanoparticles (C. Gomez-Gaete et al., International Journal of Pharmaceutics 331 (2007) 153-159). However, the highest drug loading was obtained using 100 mg PLGA and 10 mg of dexamethasone, corresponding to a dexamethasone loading of 0.2% w/w, which remains too low to achieve high concentration of glucocorticoids. Moreover, the in vitro study indicates a burst release of dexamethasone, which should be avoided.

The design of nanoparticles encapsulating glucocorticoids to modify the pharmacokinetics of the active substance is still highly needed. These nanoparticles should have a high drug loading, a favorable pharmacokinetics while limiting the burst release and reducing systemic side effects.

SUMMARY

This invention thus relates to a nanoparticle comprising a glucocorticoid prodrug and a surface coating material, the nanoparticle size is ranging from 20 to 400 nm and the glucocorticoid prodrug loading is higher than 10% in weight to the weight of nanoparticle.

According to one embodiment, the nanoparticle comprising a glucocorticoid prodrug and a surface coating material, the nanoparticle size is ranging from 20 to 400 nm; wherein the glucocorticoid prodrug is a lipophilic long-chain ester of a glucocorticoid; wherein the glucocorticoid prodrug is in an amorphous state; and wherein the glucocorticoid prodrug loading is higher than 10% in weight to the weight of nanoparticle.

According to one embodiment, the glucocorticoid released is a dexamethasone derivative.

According to one embodiment, the glucocorticoid prodrug is a lipophilic derivative of a glucocorticoid.

According to one embodiment, the glucocorticoid prodrug is dexamethasone palmitate.

According to one embodiment, the glucocorticoid prodrug is a lipophilic long-chain ester of dexamethasone.

According to one embodiment, the surface coating material is selected from poloxamer 407, poloxamer 188, polyoxyethylene (40) monostearate, polysorbate 20, polysorbate 80, tyloxapol, polyoxyl (40) hydrogenated castor oil (cremophor RH 40), Polyoxyl (35) hydrogenated castor oil (cremophor EL), Tocopherol polyethylene glycol succinate (vitamin E TGPS), 1,2-distearoyl-sn-glycero-3-phosphoethanolamine-N-[amino(polyethylene glycol)-2000] (ammonium salt) (DSPE-PEG) and polyvinyl alcohol (PVA).

According to one embodiment, the surface coating material is DSPE-PEG.

According to one embodiment, the glucocorticoid prodrug is in an amorphous state.

According to one embodiment, the nanoparticle has polyoxyethylene (PEG) surface density smaller than 0.30 nm$^2$ per polyoxyethylene chain.

This invention thus relates to a medicament comprising at least one nanoparticle of the invention.

This invention thus relates to a pharmaceutical composition comprising at least one nanoparticle of the invention and at least one pharmaceutically acceptable excipient.

According to one embodiment, the pharmaceutical formulation is formulated for intravenous (IV) administration.

This invention thus relates to a nanoparticle of the invention for use in the treatment of inflammatory diseases or conditions.

According to one embodiment, the inflammatory disease is selected from rheumatoid arthritis, ankylosing spondylitis, psoriatic arthritis and lupus erythematous.

This invention thus relates to a kit comprising a container containing a pharmaceutical composition of the invention.

This invention thus relates to a process for manufacturing at least one nanoparticle of the invention, wherein the process for manufacturing is a nanoprecipitation process or an emulsion-evaporation process, starting from a solution of glucocorticoid prodrug and surface coating material in volatile solvent and aqueous solution, preferably water, or from a solution of glucocorticoid prodrug in volatile solvent and a aqueous solution of surface coating material, preferably a water solution of surface coating material.

Definitions

In the present invention, the following terms have the following meanings:

"alkyl" refers to a linear or branched saturated hydrocarbon with 1 to 20 carbon atoms, preferably 10 to 20 carbon atoms. Non-limiting examples of alkyl groups are methyl, ethyl, propyl, butyl, pentyl, hexyl, heptyl, octyle, nonyl, decyl, undecyl, dodecyl, tridecyl, tetradecy, pentadecyl, hexadecyl, heptadecyl, octadecyl, nonadecyl, preferably undecyl, tridecyl, pentadecyl, heptadecyl.

"alkenyl" refers to a linear or branched hydrocarbon chain having at least one double bond, of 2 to 20 carbon atoms, and preferably 2 to 10 carbon atoms. Non-limiting examples of alkenyl groups are ethenyl, propenyl, butenyl, pentenyl and hexenyl.

"amorphous state" refers to a solid state of matter with two characteristics: (1) the properties of a substance in the amorphous state (mechanical, thermal, electrical, and so forth) are ordinarily independent of the direction of measurement in the substance (isotropy) and (2) with increased temperature, the substance softens and enters the liquid state only gradually. In other words, there is no definite melting point in the amorphous state. These characteristics result from the absence of long-range order in the amorphous state.

"amorphous compound" refers to compound that lacks the long-range order characteristic of a crystal and which is in an amorphous state.

"approximately" and "about", as used herein in reference to a number, generally includes numbers that fall within a range of 10% in either direction of the number (greater than or less than the number) unless otherwise stated or otherwise evident from the context (except where such a number would exceed a possible value).

"corticosteroid" refers to any of a wide variety of drugs that are closely related to cortisol, a hormone which is naturally produced in the adrenal cortex. Examples of corticosteroids include, but are not limited to, alclometasone, amcinonide, amcinafel, amcinafide, beclamethasone, betamethasone, ciclesonide, clobetasone, chloroprednisone, clocortelone, cortisol, C21-desmethylpropionyl-ciclesonide, cortodoxone, difluorosone, descinolone, desonide, defluprednate, dihydroxycortisone, desoximetasone, dexamethasone, deflazacort, diflorasone, dichlorisone, fluazacort, flucetonide, flucloronide, fludrotisone, fluorocortisone, flumethasone, flunisolide, fluocinonide, fluocinolone, flucortolone, fluperolone, fluprednisolone, fluroandrenolone, flurandrenolide, fluorametholone, fluticasone, hydrocortisone, hydrocortamate, loteprendol, medrysone, meprednisone, methylprednisone, methylprednisolone, mometasone, paramethasone, prednisolone, and triamcinolone.

"effective amount", refers to any amount of a compound, agent or formulation that is sufficient to fulfill its intended purpose(s), e.g., a desired biological or medicinal response in a tissue, system or subject. For example, in certain embodiments of the present invention, the purpose(s) may be: to slow down or stop the progression, aggravation, or deterioration of the symptoms of inflammatory disease or condition, to bring about amelioration of the symptoms of the disease or condition, and/or to cure the disease or condition. Determination of an effective amount is well within the ordinary skill in the art of pharmaceutical sciences and medicine, in that it may depend on various biological factors or individual variations and response to treatments.

"glucocorticoid" refers to a class of corticosteroids, which are a class of steroid hormones. Glucocorticoids are corticosteroids that bind to the glucocorticoid receptor (GR) that is present in almost every vertebrate animal cell. Examples of glucocorticoids include, but are not limited to, cortisone, hydrocortisone, prednisone, prednisolone, methyl-prednisolone, triamcinolone, dexamethasone, betamethasone, cortivazol, beclometasone, budesonide, fluticasone, tixocortol, flunisolide, mometasone, fluocinonide, amcinonide, fluocinolone, fluocortolone, clobétasol, desonide, fluorométholone, riméxolone, aldosterone, and ciclesonide.

"lipophilic", when used herein to characterize a compound, refers to the ability of a chemical compound to dissolve more readily in fats, oils, lipids, and non-polar solvents than in water.

"lipophilic long-chain ester of a corticosteroid" refers to a chemical entity comprising an ester function, —COO—, wherein one of the carbon or oxygen linking atoms is covalently attached to a alkyl or alkenyl chain comprising more than 11 carbon atoms, such as 13 carbon atoms, 15 carbon atoms, 17 or more, and wherein the other of the carbon and oxygen atoms is covalently attached to a functional group of the corticosteroid compound.

"nanoparticle" refers to a nanometer-sized particle wherein at least one dimension of the particle is comprised between 10 nm and 800 nm. According to one embodiment, the nanometer-sized particle has a spherical shape. In the invention, the nanoparticle comprises a corticosteroid prodrug or a glucocorticoid prodrug and a surface coating material.

"nanoparticle size" refers to the hydrodynamic diameter of the nanoparticles.

"PEG chain density" refers to the available surface of PEG chain on the surface of the nanoparticles.

"pharmaceutically acceptable carrier or excipient" refers to a carrier medium which does not interfere with the effectiveness of the biological activity of the active ingredient(s) and which is not excessively toxic to the host at a concentration at which it is administered. The term includes solvents, dispersion media, antibacterial and antifungal agents, isotonic agents, adsorption delaying agents, and the like. The use of such media and agents for pharmaceutically active substances is well known in the art (see, for example, "Remington's Pharmaceutical Sciences", E. W. Martin, 18th Ed., 1990, Mack Publishing Co.: Easton, Pa., which is incorporated herein by reference in its entirety).

"physiologically acceptable salt" refers to any acid addition or base addition salt that retains the biological activity and properties of the corresponding free base or free acid, respectively, and that is not biologically or otherwise undesirable. Acid addition salts are formed with inorganic acids (e.g., hydrochloric, hydrobromic, sulfuric, nitric, phosphoric acids, and the like); and organic acids (e.g., acetic, propionic, pyruvic, maleic, malonic, succinic, fumaric, tartaric, citric, benzoic, mandelic, methanesulfonic, ethanesulfonic, p-toluenesulfonic, salicylic acids, and the like). Base addition salts can be formed with inorganic bases (e.g., sodium, potassium, lithium, ammonium, calcium, magnesium, zinc, aluminium salts, and the like) and organic bases (e.g., salts of primary, secondary and tertiary amines, substituted amines including naturally occurring substituted amines, cyclic amines, and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexyl-amine, lysine, arginine, histidine, caffeine, procaine, hydrabanine, choline, betaine, ethylene-diamine, glycosamine, methylglucamine, theobromine, purines, piperazine, N-ethylpiperidine, polyamine resins, and the like).

"poloxamer" refers to nonionic triblock copolymers composed of a central hydrophobic chain of polyoxypropylene (poly(propylene oxide)) flanked by two hydrophilic chains of polyoxyethylene (poly(ethylene oxide)). These copolymers have the general formula H(OCH2CH2)x(OCH(CH3)CH2)y(OCH2CH2)xOH or in order to simplify (EO)x(PO)y(EO) with x in the range from 2 to 130 and preferably in a range of 15 to 67. The first two digits×100 give the approximate molecular weight of the central block, and last digit×10 gives the weight ratio of ethylene oxide units in the molecule [ex.: poloxamer 407 (tradename Pluronic F127) with a molecular weight of the central block of 4000 g·mol$^{-1}$ and a weight ratio of ethylene oxide units of 70%. Examples of poloxamer include, but are not limited to, poloxamer 407 and poloxamer 188.

"polysorbate" refers to oily liquids derived from ethoxylated sorbitan (a derivative of sorbitol) esterified with fatty acids. Examples of polysorbate include, but are not limited to, polysorbate 20 (polyoxyethylene (20) sorbitan monolaurate) and polysorbate 80 (polyoxyethylene (20) sorbitan monooleate). The number following the polyoxyethylene part refers to the total number of oxyethylene —(CH$_2$CH$_2$O)— groups found in the molecule. The number following the polysorbate part is related to the type of fatty acid associated with the polyoxyethylene sorbitan part of the molecule. Monolaurate is indicated by 20, monopalmitate is indicated by 40, monostearate by 60, and monooleate by 80.

"prodrug" refers to a compound that acts as a drug precursor which, following administration, is converted to and/or releases the pharmaceutically active drug. Conversion or release may occur via a chemical or physiological process (e.g., upon being brought to a physiological pH or through enzyme activity). Conversion or release may occur prior to, during, or following absorption, or at a specific target site of the body. Prodrugs are generally characterized by increased bioavailability and are readily metabolized into biologically active compounds in vivo.

"corticosteroid prodrug" refers to the pharmacologically acceptable derivatives of corticosteroid.

"glucocorticoid prodrug" refers to the pharmacologically acceptable derivatives of glucocorticoid.

"subject" and "individual" are used herein interchangeably. They refer to a human or another mammal (e.g., mouse, rat, rabbit, dog, cat, cattle, swine, sheep, horse or primate) that can be afflicted with or is susceptible to inflammatory disease or condition but may or may not have the disease or condition. In many embodiments, the subject is a human being. The terms "individual" and "subject" do not denote a particular age, and thus encompass adults, children, and newborns.

"surface coating material" refers to a material that functions to slow down release of the therapeutic agent from the nanoparticle.

"treatment" is used herein to characterize a method or process that is aimed at (1) delaying or preventing the onset of a disease or condition (in particular an inflammatory disease or condition); (2) slowing down or stopping the progression, aggravation, or deterioration of the symptoms of the disease or condition; (3) bringing about amelioration of the symptoms of the disease or condition; or (4) curing the disease or condition. A treatment may be administered prior to the onset of the disease or condition, for a prophylactic or preventive action. Alternatively or additionally, a treatment may be administered after initiation of the disease or condition, for a therapeutic action.

"therapeutic agent", "drug", and "pharmaceutically active substance" are used herein interchangeably. They refer to a substance, molecule, compound, agent, factor or formulation effective in the treatment of a disease or condition.

DETAILED DESCRIPTION

Nanoparticle

In a first aspect, this invention relates to a nanoparticle comprising a therapeutic agent and a surface coating material.

According to one embodiment, the therapeutic agent is a prodrug. According to one embodiment, the therapeutic agent is a corticosteroid prodrug. According to one embodiment, the therapeutic agent is a glucocorticoid prodrug.

Corticosteroid prodrugs suitable for use in the practice of the present invention include any molecule which may be converted to and/or releases a corticosteroid via a chemical or physiological process following intravenous (IV) administration. Examples of corticosteroids that can be released by a corticosteroid prodrug according to the present invention include, but are not limited to, alclometasone, amcinonide, amcinafel, amcinafide, beclamethasone, betamethasone, ciclesonide, clobetasone, chloroprednisone, clocortelone, cortisol, C21-des-methylpropionyl-ciclesonide, cortodoxone, difluorosone, descinolone, desonide, defluprednate, dihydroxycortisone, desoximetasone, dexamethasone, deflazacort, diflorasone, dichlorisone, fluazacort, flucetonide, flucloronide, fludrotisone, fluorocortisone, flumethasone, flunisolide, fluocinonide, fluocinolone, flucortolone, fluperolone, fluprednisolone, fluroandrenolone, flurandrenolide, fluorametholone, fluticasone, hydrocortisone, hydrocortamate, loteprendol, medrysone, meprednisone, methylprednisone, methylprednisolone, mometasone, paramethasone, prednisolone, and triamcinolone, physiologically acceptable salts thereof, derivatives thereof, and any combinations thereof.

Glucocorticoids prodrugs suitable for use in the practice of the present invention include any molecule which is converted to and/or releases a glucocorticoid via a chemical or physiological process following intravenous administration. Examples of glucocorticoids that can be released by a glucocorticoid prodrug according to the present invention include, but are not limited to, cortisone, hydrocortisone, prednisone, prednisolone, methyl-prednisolone, triamcinolone, dexamethasone, betamethasone, cortivazol, beclometasone, budesonide, fluticasone, tixocortol, flunisolide, mometasone, fluocinonide, amcinonide, fluocinolone, fluocortolone, clobétasol, desonide, fluorométholone, rimexolone, aldosterone, and ciclesonide, physiologically acceptable salts thereof, derivatives thereof, and any combinations thereof.

In certain embodiments, the corticosteroid released by a corticosteroid prodrug is selected from the group consisting of ciclesonide, triamcinolone and dexamethasone, physiologically acceptable salts thereof, derivatives thereof, and any combinations thereof. In certain preferred embodiments, the corticosteroid is dexamethasone, a physiologically acceptable salt thereof.

In certain embodiments, a corticosteroid prodrug according to the present invention comprises a lipophilic derivative of a corticosteroid.

Thus, in certain preferred embodiments, a corticosteroid prodrug or glucocorticoid prodrug of the present invention comprises an ester group. More preferably, a corticosteroid or glucocorticoid prodrug comprises a lipophilic long-chain ester of a corticosteroid or glucocorticoid. Preferred lipophilic long-chain esters of corticosteroids or glucocorticoid comprise an ester function and have one of the following formula: LLC-COO—R or R—COO-LLC, wherein LLC is a lipophilic long chain and R is a corticosteroid moiety. LLC may be any suitable lipophilic long chain. For example, LLC may be a long linear or branched alkyl or alkenyl chain, e.g., a C4-C20 alkyl chain or a C11, C13, C15, C17 or C19 saturated alkyl chain or unsaturated alkenyl chain. In certain preferred embodiments, LLC is a C11, C13, C15 or C17 alkyl chain. In certain preferred embodiments, LLC is a C15 alkyl chain. In certain preferred embodiments, the lipophilic derivative of a corticosteroid is an oleate derivative, stearate derivative, palmitate derivative or a laurate derivative. In a preferred embodiment, the lipophilic derivative of a corticosteroid is a palmitate derivative.

In certain embodiments, the glucocorticoid prodrug is dexamethasone palmitate.

Corticosteroid prodrugs of the present invention may be synthesized using methods and procedures known in the art or may be purchased from commercial sources and optionally purified before formulation and/or administration.

According to one embodiment, the nanoparticle comprises at least one therapeutic agent. According to one embodiment, the nanoparticle comprises two or more different therapeutic agents. In one embodiment two or more therapeutic agents are combined into and delivered from one nanoparticle. According to one embodiment, the additional therapeutic agents are corticosteroids and/or corticosteroids prodrugs.

According to one embodiment, the therapeutic agent loading is higher than 10% w/w, preferably higher than 25%, more preferably higher than 40% in weight to the weight of nanoparticle.

The surface coating material can be formed of non-biodegradable and/or biodegradable materials, although biodegradable materials are often preferred.

The surface coating material may be polyvinyl alcohols, poloxamer, tyloxapol, castor oil derivatives, lipids, polysorbate, Vitamin E derivatives, PEG-40 stearate or a combination thereof.

In one embodiment the surface coating material represents at least 15% w/w in weight to the weight of nanoparticle. The content of surface coating material in the nanoparticle can be ranging from 30% and about 90% w/w in weight to the weight of nanoparticle. In typical embodiments, the surface coating material is present in an amount ranging from 40% and 70% w/w in weight to the weight of nanoparticle.

Representative lipids include the following classes of molecules: fatty acids and derivatives, mono-, di- and triglycerides, phospholipids, sphingolipids, cholesterol and steroid derivatives, terpenes, and vitamins. Fatty acids and derivatives thereof may include saturated and unsaturated fatty acids, odd and even number fatty acids, cis and trans isomers, and fatty acid derivatives including alcohols, esters, anhydrides, hydroxy fatty acids and prostaglandins. Saturated and unsaturated fatty acids that may be used include molecules that have between 12 carbon atoms and 22 carbon atoms in either linear or branched form. Examples of saturated fatty acids that may be used include lauric, myristic, palmitic, and stearic acids. Examples of unsaturated fatty acids that may be used include lauric, physeteric, myristoleic, palmitoleic, petroselinic, and oleic acids. Examples of branched fatty acids that may be used include isolauric, isomyristic, isopalmitic, and isostearic acids and isoprenoids. Fatty acid derivatives include 12-(((7'-diethylaminocoumarin-3 yl)carbonyl)methylamino)-octadecanoic acid; N-[12-(((7'diethylaminocoumarin-3-yl) carbonyl)methylamino) octadecanoyl]-2-aminopalmitic acid, N succinyl-dioleoylphosphatidylethanol amine and palmitoyl-homocysteine; and/or combinations thereof. Mono, di- and triglycerides or derivatives thereof that may be used include molecules that have fatty acids or mixtures of fatty acids between 6 and 24 carbon atoms, digalactosyldiglyceride, 1,2-dioleoyl-sn-glycerol; 1,2-dipalmitoyl-sn-3 succinylglycerol; and 1,3-dipalmitoyl-2-succinylglycerol.

In one preferred embodiment, the surface coating material comprises a phospholipid or combinations of phospholipids. Phospholipids that may be used include phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Examples of phosphatidylcholines include such as dioleoylphosphatidylcholine, dimyristoylphosphatidylcholine (DMPC), dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) may also be used. Examples of phosphatidylethanolamines include dicaprylphosphatidylethanolamine, dioctanoylphosphatidylethanolamine, dilauroylphosphatidylethanolamine, dimyristoylphosphatidylethanolamine (DMPE), dipalmitoylphosphatidylethanolamine (DPPE), dipalmitoleoylphosphatidylethanolamine, distearoylphosphatidylethanolamine (DSPE), dioleoylphosphatidylethanolamine, and dilineoylphosphatidylethanolamine. Examples of phosphatidylglycerols include dicaprylphosphatidylglycerol, dioctanoylphosphatidylglycerol, dilauroylphosphatidylglycerol, dimyristoylphosphatidylglycerol (DMPG), dipalmitoylphosphatidylglycerol (DPPG), dipalmitoleoylphosphatidylglycerol, distearoylphosphatidylglycerol (DSPG), dioleoylphosphatidylglycerol, and dilineoylphosphatidylglycerol. Preferred phospholipids include DMPC, DPPC, DAPC, DSPC, DTPC, DBPC, DMPG, DPPG, DSPG, DMPE, DPPE, and DSPE.

Additional examples of phospholipids include modified phospholipids for example phospholipids having their head group modified, e.g., alkylated or polyethylene glycol (PEG)-modified, hydrogenated phospholipids, phospholipids with multifarious head groups (phosphatidylmethanol, phosphatidylethanol, phosphatidylpropanol, phosphatidylbutanol, etc.), dibromo phosphatidylcholines, mono and diphytanoly phosphatides, mono and diacetylenic phosphatides, and PEG phosphatides.

Examples of preferred phospholipids include DSPE-PEG$_{500}$, DSPE-PEG$_{1000}$, DSPE-PEG$_{2000}$, DSPE-PEG$_{5000}$, DSPE-PEG$_{10000}$, DPPE-PEG$_{500}$, DPPE-PEG$_{1000}$, DPPE-PEG$_{2000}$, DPPE-PEG$_{5000}$ and DPPE-PEG$_{1000}$; preferably phospholipids include DSPE-PEG$_{2000}$ and DPPE-PEG$_{2000}$. The number following the PEG is related to PEG chain molecular weight. The DSPE-PEG 2000, chemical name N-(Carbonyl-methoxypolyethyleneglycol 2000)-1,2-distearoyl-sn-glycero-3-phosphoethanolamine, sodium salt, has a PEG chain molecular weight of 2000 g·mol$^{-1}$.

Examples of poloxamers that may be used include but are not limited to poloxamer 407, poloxamer 188, poloxamer 124, poloxamer 237, poloxamer 338. Examples of preferred poloxamers include poloxamer 407 and poloxamer 188.

Examples of castor oil derivatives, that may be used include but are not limited to PEG-35 castor oil, PEG-40 castor oil.

Examples of polysorbates that may be used include but are not limited to polysorbate 20, polysorbate 40, polysorbate 60, polysorbate 80. Examples of preferred polysorbates include polysorbate 20 and polysorbate 80.

Vitamin E derivatives that may be used are water soluble derivatives of natural Vitamin E. Example of Vitamin E derivatives that may be used include but are not limited to Vitamin E TPGS 400 (Tocopherol polyethylene glycol 400 succinate), Vitamin E TPGS 1500 (Tocopherol polyethylene glycol 1500 succinate), and Vitamin E TPGS 2000 (Tocopherol polyethylene glycol 2000 succinate).

According to a preferred embodiment, the surface coating material is selected from poloxamer 407, poloxamer 188, PEG-40 stearate, polysorbate 20, polysorbate 80, tyloxapol, PEG-40 castor oil (cremophor RH 40), PEG-35 castor oil (cremophor EL), vitamin E TGPS, DSPE-PEG, DPPE-PEG and PVA; Preferably, the surface coating material is selected from DSPE-PEG, DPPE-PEG, Poloxamer 407 or 188, polyvinyl alcohol (PVA), PEG-40-Stearate and any combination thereof. According to one embodiment, the surface coating material is DSPE-PEG, PVA or Poloxamer 407. According to a preferred embodiment, the surface coating material is DSPE-PEG.

According to one embodiment, the nanoparticle of the invention has a particle size distribution ranging from 10 nm to 800 nm, preferably from 10 nm to 500 nm, more preferably from 20 nm to 400 nm and even more preferable from 30 nm to 250 nm.

According to one embodiment, the therapeutic agent may be present in an amorphous state, a crystalline state, or a mixture thereof. According to one embodiment, the therapeutic agent is mainly present in an amorphous state. According to one embodiment, the therapeutic agent is only present in an amorphous state. According to one embodiment, the therapeutic agent is mainly present in an amorphous state after storage at 4° C. for at least 2 weeks, preferably for at least 3 weeks.

According to one embodiment, the nanoparticle has a PEG chain density smaller than 0.30 $nm^2$ per PEG chain, preferably smaller than 0.4 $nm^2$ per PEG chain, more preferably smaller than 0.45 $nm^2$ per PEG chain.

According to one embodiment, the nanoparticle of the invention is not porous. According to one embodiment, the nanoparticle of the invention is not a liposome.

Process of Manufacturing

The invention also relates to a process of manufacturing at least one nanoparticle of the invention.

In typical embodiments, the at least one nanoparticle is obtained by a nanoprecipitation or by emulsion-evaporation.

In one embodiment the nanoparticle is made by a method of emulsion-evaporation that includes the following steps:
(1) dissolving the surface coating material and the therapeutic agent in a volatile solvent to form a surface coating material and therapeutic agent solution;
(2) adding the solution of surface coating material and therapeutic agent in an aqueous solvent, preferably water, and emulsifying to form an emulsion; and
(3) removing the volatile solvent from the emulsion to yield at least one nanoparticle which comprises the therapeutic agent and the surface coating material.

In another embodiment the nanoparticle is made by a method of emulsion-evaporation that includes the following steps:
(1) dissolving the therapeutic agent in a volatile solvent to form a therapeutic agent solution;
(2) dissolving the surface coating material in a an aqueous solvent, preferably water, to form a aqueous surface coating material solution;
(3) adding the solution of therapeutic agent to the aqueous surface coating material solution;
(4) emulsifying to form an emulsion; and
(5) removing the volatile solvent, from the emulsion to yield at least one nanoparticle which comprises the therapeutic agent and the surface coating material.

In another embodiment the nanoparticle is made by a method of nanoprecipitation that includes the following steps:
(1) dissolving the therapeutic agent and the surface coating material in a volatile solvent to form a therapeutic agent solution;
(2) adding the solution of surface coating material and therapeutic agent in an aqueous solvent, preferably water;
(3) after precipitation of at least one nanoparticle of surface coating material and therapeutic agent, removing the volatile solvent, to yield at least one nanoparticle which comprises the therapeutic agent and the surface coating material.

In another embodiment the at least one nanoparticle is made by a method of nanoprecipitation that includes the following steps:
(1) dissolving the therapeutic agent in a volatile solvent to form a therapeutic agent solution;
(2) adding the therapeutic agent solution to a solution of surface coating material comprising surface coating material dissolved in water;
(3) after precipitation of at least one nanoparticle of surface coating material and therapeutic agent;
(4) removing the volatile solvent, to yield at least one nanoparticle which comprise the therapeutic agent and the surface coating material.

In one embodiment, the surface coating material comprises a biocompatible synthetic polymer, and/or the volatile solvent comprises an organic solvent.

A solvent for the surface coating material is selected based on its biocompatibility as well as the solubility of the surface coating material and where appropriate, interaction with the therapeutic agent to be delivered. For example, the ease with which the surface coating material is dissolved in the solvent and the lack of detrimental effects of the solvent on the therapeutic agent to be delivered are factors to consider in selecting the surface coating material solvent. Organic solvents will typically be used to dissolve hydrophobic and some hydrophilic surface coating materials. Combinations of aqueous and organic solvents may be used. Preferred organic solvents are volatile or have a relatively low boiling point or can be removed under vacuum and which are acceptable for administration to humans in trace amounts, such as dichloromethane. Other solvents, such as ethyl acetate, ethanol, methanol, dimethyl formamide (DMF), acetone, acetonitrile, tetrahydrofuran (THF), acetic acid, dimethyl sulfoxide (DMSO) and chloroform, and combinations thereof, also may be utilized. According to one embodiment, the organic solvent used is selected from dichloromethane, chloroform and acetone. According to one embodiment the organic solvent is dichloromethane. According to another embodiment the organic solvent is acetone. According to another embodiment the organic solvent is chloroform.

In general, the surface coating material is dissolved in the volatile solvent to form a surface coating material solution having a concentration of between 0.1 and 10% weight to the total volume of the solution (w/v), more preferably between 1 and 3%.

Uses

The invention is further directed to the use of nanoparticles of the invention as medicament.

The invention is further directed to a medicament comprising at least one nanoparticle of the invention, active ingredient.

The invention also provides pharmaceutical compositions comprising a nanoparticle of the invention and at least one pharmaceutically acceptable carrier. The invention also provides pharmaceutical compositions of corticosteroid prodrugs comprising at least one nanoparticle of the invention. In one embodiment corticosteroid prodrugs are glucocorticoid prodrugs. In another embodiment, the pharmaceutical composition comprises a mixture of two or more different nanoparticles each containing a different therapeutic agent.

By means of non-limiting examples, the nanoparticles of the invention may be formulated as a pharmaceutical composition in a form suitable for parenteral administration (such as by intravenous, intramuscular or subcutaneous injection or intravenous infusion). Such suitable administration forms as well as methods and carriers, diluents and excipients for use in the preparation thereof, will be clear to the skilled person; reference is made to the latest edition of Remington's Pharmaceutical Sciences. In a preferred embodiment the pharmaceutical composition of corticosteroid prodrugs is formulated for IV administration. In one embodiment corticosteroid prodrugs are glucocorticoid prodrugs.

Some non-limiting examples of such preparations include sterile injectable solutions for administration as a bolus and/or for continuous administration, which may be formulated with carriers, excipients, and diluents that are suitable per se for such formulations. In one embodiment, excipients suitable for injections are present in the pharmaceutical composition. In one embodiment the composition comprises excipients for the establishment of isotonic conditions, for example ionic excipients, for example sodium chloride, or other water-soluble excipients of pharmaceutically acceptable hexose types, for example sorbitol, mannitol, glucose, lactose or sorbitan.

In another aspect, the present invention relates to pharmaceutical kits. A pharmaceutical kit according to the present invention comprises one or more containers (e.g., IV bag, vials, ampoules, flasks, or bottles) containing one or more ingredients of an inventive composition, allowing administration of the composition to a subject. Such containers may be made of glass, plastic materials, resins, and the like. They may be transparent or, alternatively, they may be colored or opaque to prevent or reduce the risk that active ingredients be directly exposed to light. In certain embodiments, a container is in a form that allows IV administration of an inventive composition.

In certain embodiments, a pharmaceutical kit includes one or more additional approved therapeutic agents as described above. Optionally associated with such container(s) can be a notice or package insert in the form prescribed by a governmental agency regulating the manufacture, use or sale of pharmaceutical or biological products, which notice reflects approval by the agency of manufacture, use or sale for human administration. The notice or package insert may contain instructions for use of a pharmaceutical composition according to methods disclosed herein.

An identifier, e.g., a bar code, radio frequency, ID tags, etc., may be present in or on the kit. The identifier can be used, for example, to uniquely identify the kit for purposes of quality control, inventory control, tracking movement between workstations, etc.

According to one embodiment, the pharmaceutical formulation of the invention releases a therapeutically or prophylactically effective amount of the drug from the at least one nanoparticle in the body for at least 2 hours, preferably for at least 3 h, more preferably for at least 5 h.

Nanoparticles of the invention are useful for the treatment of inflammatory diseases or conditions.

The invention also relates to composition comprising an effective amount of nanoparticles of the invention for use in the treatment of inflammatory diseases or conditions.

The invention further provides the use of a nanoparticle according to the invention for the manufacture of a medicament for the treatment and/or prevention inflammatory diseases or conditions.

According to one embodiment, "inflammatory diseases or conditions" include: wide variety of inflammatory diseases or conditions.

The invention further relates to a method for treating and/or preventing inflammatory diseases or conditions which comprises administering to a subject in need thereof a therapeutically effective amount of a nanoparticle according to the invention.

The pharmaceutical composition according to the present invention may be used in a method for treatment of the human or animal.

In one aspect, the pharmaceutical composition according to the present invention may be used in a method for treating an inflammatory condition through IV-administration of said composition.

In another aspect, the present invention relates to methods for the treatment inflammatory diseases or conditions. Such methods comprise a step of IV administering of an effective amount of a nanoparticle as described herein, or a pharmaceutical formulation thereof.

Inflammatory diseases or conditions may be any of a wide variety of acute and chronic inflammatory diseases or autoimmune diseases such as rheumatoid arthritis, ankylosing spondylitis, psoriatic arthritis or lupus erythematus.

A treatment according to the present invention may consist of a single dose or a plurality of doses over a period of time. Administration may be one or multiple times daily, weekly (or at some other multiple day interval) or on an intermittent schedule.

Optimization of the appropriate dosages can readily be made by one skilled in the art in light of pharmacokinetic data observed in clinical trials. Final dosage regimen will be determined by the attending physician, considering various factors which modify the action of the drug, e.g., the drug's specific activity, the severity of the disease or condition and the responsiveness of the patient, the age, condition, body weight, sex and diet of the patient, the severity of any present infection, time of administration, the use (or not) of concomitant therapies, and other clinical factors. As studies are conducted using formulations of the present invention, further information will emerge regarding the appropriate dosage levels and duration of treatment.

It will be appreciated that pharmaceutical formulations of the present invention can be employed alone or in combination with additional therapies. The method according to the present invention may further comprise a step of administering to the subject an effective amount of a therapeutic agent. This therapeutic agent may be administered prior to, concomitantly with, or following administration of the pharmaceutical formulation of the corticosteroid prodrug. The particular combination of therapies (therapeutics or procedures) to employ in such combination regimen will take into account compatibility of the desired therapeutics and/or procedures and the desired therapeutic effect to be achieved.

EXAMPLES

Figure 1:
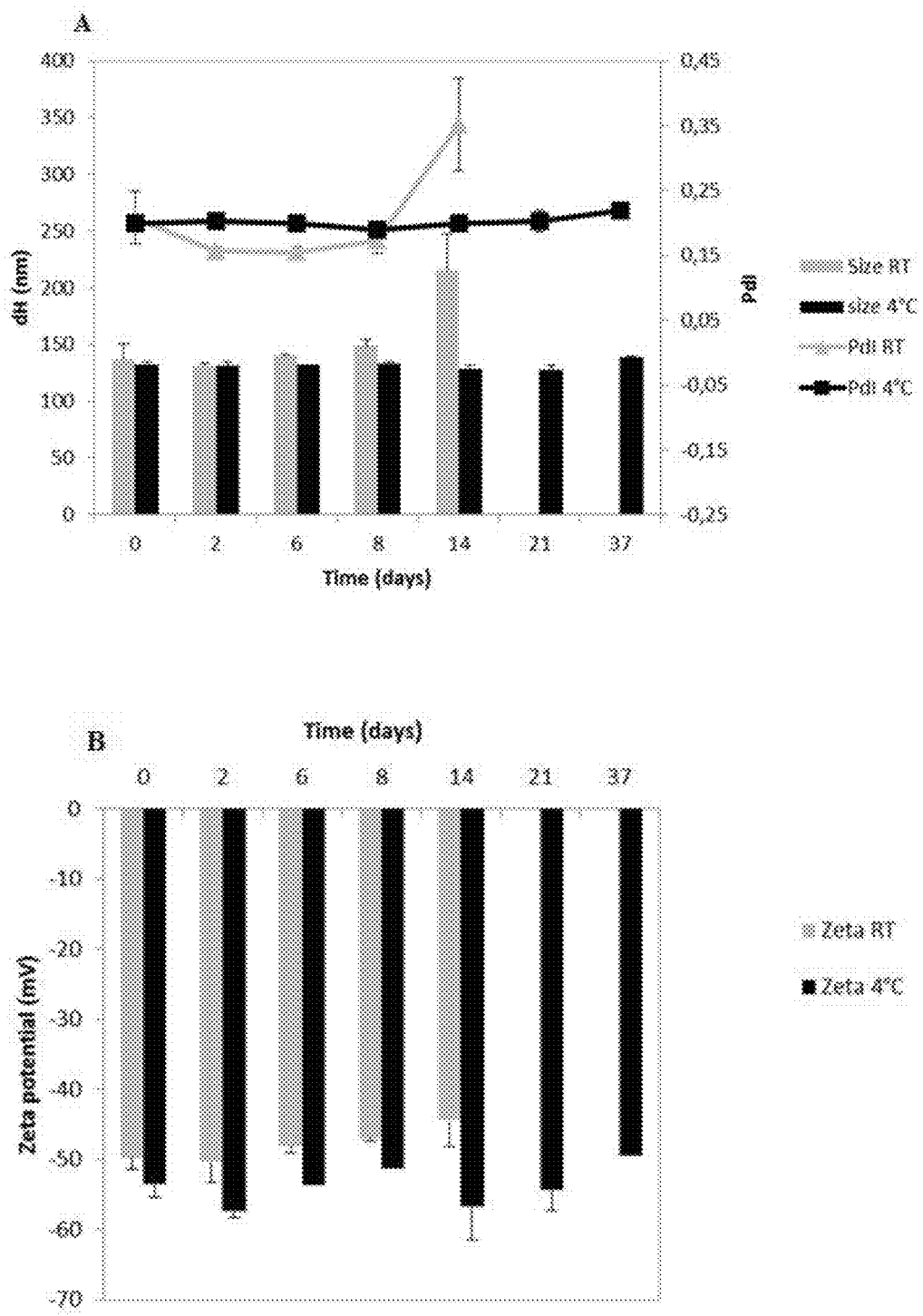
FIG. 1 is a graph showing: A: the hydrodynamic diameter overtime for nanoparticles obtained by emulsion-evaporation process at room temperature, n=4 (in grey) and at T=4° C., n=5 (in black); and the polydiversity index (PdI) for nanoparticles obtained by emulsion-evaporation process at room temperature, n=4 (in grey); and at T=4° C., n=5 (in black); B: Zeta potential overtime for nanoparticles obtained by emulsion-evaporation process at room temperature, n=3 (in grey); and at T=4° C., n=5 (in black).

The present invention is further illustrated by the following examples.

Synthesis

Abbreviations

DMSO: dimethyl sulfoxide;
DPPE: 1,2-dipalmitoyl-sn-glycero-3-phosphoethanolamine;
DPPC: 1,2-dipalmitoyl-sn-glycero-3-phosphocholine;
DSP: dexamethasone sodium phosphate;
DXM: Dexamethasone base;
DXP: Dexamethasone palmitate;
DSPE-PEG=DSPE-PEG$_{2000}$: 1,2-distearoyl-sn-glycero-3-phosphoethanolamine-N-[amino(polyethylene glycol)-2000] (ammonium salt);
EDC: 1-ethyl-3-[3-dimethyl)aminopropyl]carbodiimide;
HA: Hyaluronic acid;
IR: Infrared;
NMR: Nuclear magnetic resonance;
LPS: Lipopolysaccharide;
PBS: Phosphate-buffered saline;
PVA: polyvinyl alcohol;
PdI: Polydiversity index;
HPLC: high pressure liquid chromatography;
ZP: Zeta potential;
DLS: Dynamic light scattering.

Material

Dexamethasone was provided by CHEMOS GmbH (lot No. 051104).

The following products were obtained from Sigma-Aldrich: iron chloride (III) (Cl$_3$Fe, 6H$_2$O—lot #SZBB1020V Mw=270.3 g/mol; CAS: 10025-77-1), ammonium thiocyanate (CH$_4$N$_2$S—lot #SZBB2860V, Mw=76.12 g/mol CAS: 1762-95-4) PVA or poly (vinyl alcohol) (M=32,725 g/mol, product No. P8136, batch No. 094K0104) lauroyl chloride (ref 156930, CAS No. 112-16-3 and Lot No. BCBH4480V), stearoyl (ref 85730, CAS No. 112-76-5 and Lot No. BCBJ2523V) and oleoyl (ref 367850, CAS No. 112-77-6 and Lot No. SHBF0784V), D-(+)-trehalose dihydrate (C$_{12}$H$_{22}$O$_{11}$,2H$_2$O formula, MW=378.33 g/mol CAS: 61-38-23.4).

The dexamethasone palmitate was obtained from expert Sinochem Company Limited, batch number: 5201207133. The DSPE-PEG$_{2000}$ or 1,2-distearoyl-sn-glycero-3-phosphoethanolamine-N-(methoxy (polyethylene glycol)-2000) (ammonium salt), (MW(DSPE-PEG$_{2000}$)=2805.54 g/mol.—Ref 880120P) was provided by Avanti Polar Lipids, Inc. (Alabaster, Ala., United States).

High molecular weight hyaluronic acid (HA) (sodium salt, 1500 kDa, purity of 95%) was purchased from Acros organics (Geel, Belgium). 1,2-dipalmitoyl-sn-glycero-3-phosphocholine (DPPC), 1,2-dipalmitoyl-sn-glycero-3-phosphoethanolamine (DPPE), provided by Avanti Polar Lipids (USA), while 1-ethyl-3-[3-dimethyl)aminopropyl] carbodiimide (EDC) was obtained from Sigma.

Poloxamer 407 (Synperonic PE/F 127 Flakes, Lot No. 1905PK4060), Poloxamer 188 (Pluronic F68) and PEG-40-stearate were supplied by Croda Health Care (Snaith, UK).

The experiments were carried out where possible in amber glassware or covered with aluminum because of the photosensitivity of dexamethasone.

Methods

All compounds were fully characterized by $^1$H (400.133 or 300.135 MHz) and $^{13}$C (125.773 or 75.480 MHz) NMR spectroscopy (Bruker AC 300 and Avance DRX 400 spectrometers). Coupling constants J are given in Hertz. The following abbreviations were used: s for singlet, d doublet, t triplet, q quadruplet, qt quintuplet, m for multiplet, dd for doublet of doublets and dt for doublet of triplets.

Results

Glucocorticoid Prodrugs

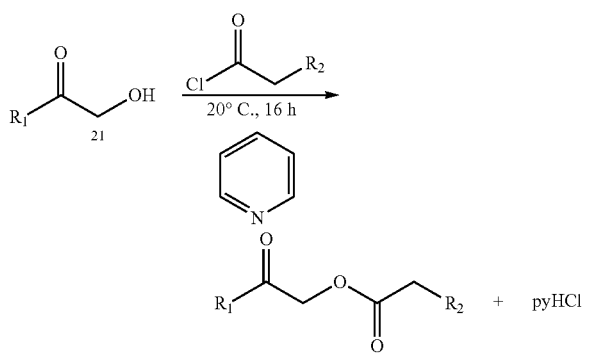

wherein R$_1$C(O)CH$_2$OH represents the drug, and R$_2$ is a C11-C17 alkyl.

Non commercially available prodrugs were synthesized by esterification of the carbon C-21 alcohol of dexamethasone by chlorides (lauric, palmitic, stearic and oleic).

To perform this synthesis, 1 mmol dexamethasone was dissolved in pyridine (6 mL/mmol for the other) and then treated with two equivalents of acyl chloride injected dropwise at 0° C. The solution was left at room temperature overnight with stirring under nitrogen. After 24 hours, pyridine was distilled under vacuum.

The solution was diluted in dichloromethane (at least 10 mL) and washed successively with about 5 mL of HCl (0.05 M), with ~5 ml of water and NaHCO$_3$ 5% (~5 mL) to neutralize acid. The organic phase was dried over anhydrous magnesium sulfate (MgSO$_4$) for 30 minutes while stirring and was then filtered and the solid rinsed with CH$_2$Cl$_2$.

For palmitates, laurates and stearates dexamethasone, the obtained product was purified by chromatography on a silica gel column, eluting with a mixture of ethyl acetate/cyclohexane at a ratio of 1/4 then with 1/2.

The product-containing fractions were then collected in a tared flask and the solvent was evaporated on rotavapor in a bath at 40° C. then placed under vacuum at 0.05 mmHg. After weighing the products were taken up in dichloromethane and each placed in a vial. The flasks were left under the hood for 2 or 3 days until evaporation of the dichloromethane and then placed in vacuum dessicator with P$_2$O$_5$ for at least a day. For some products, such as dexamethasone laurate, solvent was difficult to evaporate and viscous products were obtained. Then, the flask was heated under vacuum in order to complete evaporating the CH$_2$Cl$_2$ before being placed in a desiccator.

Compound 1: 21-Lauroyl dexamethasone: Yield: 70.2%, IR (neat), v: 3600-3200, 2956, 2922, 2872, 2853, 1748, 1731, 1661, 1620, 1605, 1468, 1438, 1409, 1394, 1377, 1366, 1352, 1298, 1267, 1240, 1186, 1174, 1155, 1133, 1113, 1102, 1089, 1073, 1058, 1036, 1020, 1007, 992, 980, 970, 953, 942, 929, 911, 902, 887, 871, 851, 829, 812, 799, 778, 762, 721, 685; $^1$H NMR (400 MHz, CDCl$_3$): δ 7.20 (d, J=10.4 Hz, 1H, H-1), 6.32 (dd, J=10.4 Hz, J=1.6 Hz, 1H, H-2), 6.10 (s, 1H, H-4), 4.91 (d, J=17.2 Hz, 1H, H-21), 4.85 (d, J=17.2 Hz, 1H, H-21), 4.35 (broad d, J=8.8 Hz, 1H, H-11), 3.15-3.05 (m, 1H, H-16), 2.61 (dt, J=13.6 Hz, J=5.2 Hz, 1H, H-6β), 2.50 (s, 1H, OH), 2.45-2.30 (m, 5H, O$_2$CCH$_2$CH$_2$, H-6α, H-8, H-12), 2.15 (dt, J=12.0 Hz, J=8.4 Hz, 1H, H-14), 2.10-2.00 (broad s, 1H, OH), 1.85-1.60 (m, 6H, O$_2$CCH$_2$CH$_2$, H-7β, H-12, H-15(3), 1.53 (m, 4H, H-7α, H-19), 1.40-1.17 (m, 29H, H-15α, lauroyl chain), 1.04 (s, 3H, H-18), 0.91 (d, J=7.6 Hz, 3H, C-16 (CH$_3$)), 0.88 (t, J=6.8 Hz, 3H, CH$_2$CH$_3$); $^{13}$C NMR (100 MHz, CDCl$_3$): δ 205.0 (C, C-20), 186.8 (C, C-3), 174.0 (C, CO$_2$CH$_2$), 166.3 (C, C-5), 152.3 (CH, C-1), 129.9 (CH, C-2), 125.2 (CH, C-4), 100.3 (CF, d, J$_{CF}$=175.0 Hz, C-9), 91.3 (C, C-17), 72.2 (CH, d, J$_{CF}$=38.6 Hz, C-11), 68.4 (CH$_2$, C-21), 48.5 (C, C-13), 48.4 (C, d, J$_{CF}$=24.0 Hz, C-10), 44.1 (CH, C-14), 36.7 (CH$_2$, C-12), 36.1 (CH, C-16), 34.3 (CH, d, J$_{CF}$=19.4 Hz, C-8), 34.0 (CH$_2$, O$_2$CCH$_2$CH$_2$), 32.4 (CH$_2$, C-15), 32.0 (CH$_2$, CH$_2$CH$_2$CH$_3$), 31.1 (CH$_2$, C-6), 29.7 (6CH$_2$, lauroyl chain), 29.6 (CH$_2$, lauroyl chain), 29.5 (CH$_2$, lauroyl chain), 29.4 (CH$_2$, lauroyl chain), 29.2 (CH$_2$, lauroyl chain), 27.5 (CH$_2$, C-7), 25.0 (CH$_2$, O$_2$CH$_2$CH$_2$), 23.0 (CH$_3$, d, J$_{CF}$=5.5 Hz, C-19), 22.8 (CH$_2$, CH$_2$CH$_2$CH$_3$), 16.7 (CH$_3$, C-16 CH$_3$), 14.8 (CH$_3$, C-18), 14.2 (CH$_3$, lauroylCH$_3$); MS (ESI+) m/z (%): 613.4 (11) [M+K]$^+$, 597.6 (100) [M+Na]$^+$ 575.4 (18) [M+H]$^+$.

Compound 2: 21-Stearoyl dexamethasone: Yield: 95.0%, IR (neat), v: 3550-3000, 2964, 29162, 2872, 2849, 1748, 1703, 1666, 1621, 1605, 1471, 1463, 1454, 1411, 1394, 1377, 1354, 1348, 1314, 1298, 1278, 1260, 1241, 1222, 1203, 1186, 1174, 1155, 1133, 1114, 1102, 1073, 1059, 1036, 1020, 1007, 992, 979, 970, 953, 942, 929, 910, 888, 852, 829, 813, 777, 761, 729, 685; $^1$H NMR (400 MHz, CDCl$_3$): δ 7.20 (d, J=10.2 Hz, 1H, H-1), 6.32 (dd, J=10.2 Hz, J=1.6 Hz, 1H, H-2), 6.10 (s, 1H, H-4), 4.91 (d, J=17.2 Hz, 1H, H-21), 4.85 (d, J=17.2 Hz, 1H, H-21), 4.35 (broad d, J=8.8 Hz, 1H, H-11), 3.15-3.05 (m, 1H, H-16), 2.61 (dt, J=13.6 Hz, J=6.0 Hz, 1H, H-6β), 2.49 (s, 1H, OH), 2.45-2.30 (m, 5H, O$_2$CCH$_2$CH$_2$, H-6α, H-8, H-12), 2.15 (dt, J=12.0 Hz, J=8.4 Hz, 1H, H-14), 2.05-1.90 (broad s, 1H, OH), 1.85-1.60 (m, 6H, O$_2$CCH$_2$CH$_2$, H-7β, H-12, H-15β), 1.53 (m, 4H, H-7α, H-19), 1.40-1.17 (m, 29H, H-15α, stearoyl chain), 1.04 (s, 3H, H-18), 0.91 (d, J=7.6 Hz, 3H, C-16 (CH$_3$)), 0.87 (t, J=6.8 Hz, 3H, CH$_2$CH$_3$); $^{13}$C NMR (100 MHz, CDCl$_3$): δ 205.0 (C, C-20), 186.8 (C, C-3), 174.0 (C, CO$_2$CH$_2$), 166.2

(C, C-5), 152.3 (CH, C-1), 129.9 (CH, C-2), 125.2 (CH, C-4), 100.3 (CF, d, $J_{CF}$=175.0 Hz, C-9), 91.2 (C, C-17), 72.2 (CH, d, $J_{CF}$=38.5 Hz, C-11), 68.4 ($CH_2$, C-21), 48.5 (C, C-13), 48.4 (C, d, $J_{CF}$=24.0 Hz, C-10), 44.2 (CH, C-14), 36.7 ($CH_2$, C-12), 36.1 (CH, C-16), 34.3 (CH, d, $J_{CF}$=19.4 Hz, C-8), 34.0 ($CH_2$, $O_2CCH_2CH_2$), 32.4 ($CH_2$, C-15), 32.0 ($CH_2$, $CH_2CH_2CH_3$), 31.2 ($CH_2$, C-6), 29.8 (12$CH_2$, stearoyl chain), 29.7 ($CH_2$, stearoyl chain), 29.6 ($CH_2$, stearoyl chain), 29.5 ($CH_2$, stearoyl chain), 29.4 ($CH_2$, stearoyl chain), 29.2 ($CH_2$, stearoyl chain), 27.5 ($CH_2$, C-7), 25.0 ($CH_2$, $O_2CH_2CH_2$), 23.0 ($CH_3$, d, $J_{CF}$=5.5 Hz, C-19), 22.8 ($CH_2$, $CH_2CH_2CH_3$), 16.7 ($CH_3$, C-16 $CH_3$), 14.7 ($CH_3$, C-18), 14.1 ($CH_3$, stearoyl$CH_3$); MS (APCI+) m/z (%): 658.7 (100) $[M+H]^+$, 639.5 (50) $[M+H—H_2O]^+$, 621.5 (12) $[M+H]^+$.

HA-DPPE

Hyaluronic acid lipidic conjugate (HA-DPPE) was synthesized as described by Surace et al., with some modifications (Surace et al., *Molecular Pharmaceutics* 6(4) (2009) 1062-1073). Briefly, HA (14 mg) was dissolved into distilled water and pre-activated with EDC at pH 4 adjusted by titration with HCl 0.1 N. Subsequently, DPPE (360 µg) was added to the HA solution and the pH was adjusted at 8.6 with a 0.1 M borate buffer pH 9.4. The reaction was let to proceed for 24 h at 37° C. The final product was purified by ultrafiltration and dialysis (Spectra/Por regenerated cellulose membrane with a molecular cutoff of 50,000). Reaction was monitored by thin layer chromatography (TLC) using F254 silica gel precoated sheets (Saint-Quentin-Fallavier, France). After migration of the mobile phase ($CHCl_3/CH_3OH$ 2:1 v/v), sheets were exposed to iodine vapors, solutions of molybdenum blue and ninhydrin (2,2-dihydroxyindene-1,3-dione) solution (1 mg/mL ethanol).

Formulation

Methods

Emulsification-Solvent Evaporation

DSPE-PEG2000/DXP 10 ml of milliQ water was prechilled at 4° C. The desired amounts of DXP and DSPE-$PEG_{2000}$ were dissolved in 1 ml chloroform. The organic phase was injected into the water phase thanks to a solvent-compatible syringe and 20G×2$^{3/4}$ needle. To obtain the emulsion, mixture was vortexed 30 seconds and placed under ultrasonication during 2 min at amplitude of 40% with ice bath. The evaporation of organic phase was performed under reduced pressure using a rotary evaporator. After full evaporation of the solvent, the suspension volume was completed to 10 mL with Milli-Q water in a volumetric flask and fresh nanoparticles were stored at 4° C. protected from light.

PVA/DXP

For PVA nanoparticles, the organic phase was prepared by dissolving 5 to 15 mg of the DXP in 4 mL dichloromethane. Then the aqueous phase, composed of 20 mL of 1% PVA was poured into the organic phase and the mixture is vortexed. The emulsion was placed under ultrasonication during 2 minutes at an amplitude of 30%. Evaporation of the solvent is carried out with slow stirring under the hood for at least 3 hours in a water bath of 20° C. The obtained emulsion was ultracentrifuged for 1 hour at 20000 rpm and 4° C. The supernatant was removed and the pellet resuspended in 5 ml of milli-Q water helped by vortexing. Fresh nanoparticles were stored at 4° C. protected from light.

HA-DPPE Coated Nanoparticles of DXP

DXP was solubilized in 1 mL chloroform (either at 5 or 10 mg/mL), HA-DPPE in 10 mL water at 4° C. (either at 0.5 or 1 mg/mL). DXP solution was added using a syringe to the HA-DPPE solution. The mixture was vortexed for 30 s for 5 minutes. After, sonication was performed for 1 to 2 minute at 40% amplitude. Chloroform was evaporated under reduced pressure.

Nanoprecipitation

DSPE-$PEG_{2000}$/DXP

DSPE-$PEG_{2000}$ was dissolved in milliQ water at 60° C. Under magnetic stirring, DXP was dissolved in acetone was injected into the aqueous phase thanks to a solvent-compatible syringe and 20G×2$^{3/4}$ needle. After 5 min stirring, the preparation was evaporated under reduced pressure using a rotary evaporator. After full evaporation of the solvent, the suspension volume was completed to 10 ml with Milli-Q water in a volumetric flask and fresh nanoparticles were stored at 4° C. protected from light.

Poloxamer 407 or Poloxamer 188 or PEG-40-Stearate/DXP

DXP was dissolved in acetone to form the organic phase. Poloxamer 407 or Poloxamer 188 or PEG-40-Stearate was dissolved in 5 or 10 mL of milli-Q water and stirred in a bath at 60° C.

The organic phase was then injected with a 20G needle into the aqueous phase and the emulsion was stirred for 2 minutes.

Evaporation of the solvent was done in a bath at 55° C. and the pressure is lowered step by step, to avoid foam formation, as follow:

from 556 to 400 mbar: increments of 50 mbar;

from 400 to 250 mbar: increments of 20 mbar;

From 250 to 140 mbar: increments of 5-10 mbar;

Leave 10 min at 140 mbar.

After full evaporation of the solvent, the suspension volume was completed to 10 ml with Milli-Q water in a volumetric flask and fresh nanoparticles were stored at 4° C. protected from light.

HA-DPPE Coated Nanoparticles of DXP

DXP was solubilized in 1 mL acetone (either at 5 or 10 mg/mL), HA-DPPE in 10 mL water at 60° C. (either at 0.5 or 1 mg/mL). DXP solution was added slowly using a syringe to the HA-DPPE solution. The mixture was left under magnetic stirring for 5 minutes. Acetone was then evaporated under reduced pressure.

Results

Emulsification-Solvent Evaporation

DSPE-PEG2000 Nanoparticles

Tests were conducted from a "standard" formulation, for which the settings were modified, one after another, to study their impact in terms of particle diameter, polydispersity and suspension stability. All of these results are summarized in Table 1.

A 2 minute sonication time allows to slightly reduce the size of the nanoparticles (entry 2): 130 nm instead of 140 nm.

Larger nanoparticles of about 180 nm were obtained, by varying the aqueous phase volume (entries 3, 4 and 5) by using of DSPE-$PEG_{5000}$ instead of DSPE-$PEG_{200}$ (entry 5), or when ethyl acetate replaces chloroform as solvent (entry 7). Formulation of entry 6 provides the same particle size as formulation of entry 2 but the final concentration of DXP is two times lower.

TABLE 1

Impact of formulation parameters during emulsion-evaporation nanoparticles preparation

| | DXP/ DSPE-PEG$_{2000}$ (mg/ml) | Volume CHCl$_3$-water (ml) | Sonication time (min) (Amplitude 40%) | $d_H$ (nm) | PdI | Stability D14 at room temperature |
|---|---|---|---|---|---|---|
| 1 | 5/2.5 | 1-10 | 1 | 140 | 0.14 | NO |
| 2 | 5/2.5 | 1-10 | 2 | 130 | 0.17 | NO |
| 3 | 5/2.5 | 1-2 | 1 | 180 | 0.15 | YES |
| 4 | 5/2.5 | 1-5 | 1 | 180 | 0.10 | YES |
| 5 | 5/2.5$^a$ | 1-10 | 2 | 180 | 0.16 | YES |
| 6 | 2.5/1.25 | 1-20 | 2 | 123 | 0.18 | NO |
| 7 | 5/2.5 | 1-10$^b$ | 1 | 170 | 0.16 | YES |

$^a$DSPE-PEG$_{5000}$; $^b$Ethyl Acetate-Water

HA-DPPE Coated Nanoparticles of DXP

Nanoparticles from 300 to 400 nm were obtained with a polydispersity index of 0.2 and a negative zeta potential of −30 mV. Nanoparticles were stable for about 30 days at 4° C.

Nanoprecipitation
DSPE-PEG2000 Nanoparticles

Tests were carried out by changing the final concentrations of the substances present in the formulation (DXP and DSPE-PEG$_{2000}$). For each formulation, a short test of stability over 15 days at room temperature was performed to preliminarily evaluate how these concentrations bearing on the nanoparticle size and polydispersity index.

All of the suspensions obtained are stable at least during 15 days of storage at room temperature, protected from light. The smallest hydrodynamic diameter obtained in these experiments is 230 nm (entry 2), which corresponds to the concentrations DXP/DSPE-PEG2000: 5/2.5 mg/ml.

TABLE 2

Nanoprecipitation: impact of concentrations

| | DXP (mg/ml) | DSPE-PEG$_{2000}$ (mg/ml) | $d_H$ (nm) | PdI |
|---|---|---|---|---|
| 1 | 2.5 | 2.5 | 255 | 0.10 |
| 2 | 5.0 | 2.5 | 230 | 0.06 |
| 3 | 7.5 | 2.5 | 240 | 0.05 |
| 4 | 2.5 | 5.0 | 240 | 0.10 |
| 5 | 5.0 | 5.0 | 260-270 | 0.10 |
| 6 | 7.5 | 5.0 | 270 | 0.05 |
| 7 | 2.5 | 7.5 | 250 | 0.10 |
| 8 | 5.0 | 7.5 | 240 | 0.08 |
| 9 | 7.5 | 7.5 | 260 | 0.07 |

To further decrease the size, the addition of a small amount of poloxamer 407 (0.1, 0.5, 1 and 1.5% w/v) in the aqueous phase was tested. The results are shown in Table 3.

TABLE 3

Nanoprecipitation DXP/DSPE-PEG$_{2000}$ with different amounts of Poloxamer407

| Poloxamer 407 | 0.1% | 0.5% | 1% | 1.5% |
|---|---|---|---|---|
| $d_H$ (nm) | 220 | 210 | 200 | 160 |
| PdI | 0.09 | 0.08 | 0.1 | 0.25 |
| Stability | Stable within 2 weeks | Unstable within 2 weeks | Unstable within 2 weeks | Unstable within 6 days |

It can be concluded that higher poloxamer concentration, the smallest the average hydrodynamic diameter. However, for high concentrations of poloxamer 407, it was clearly noted an increase in PdI. This high PdI number is correlated to the unstability of the nanosuspension (Table 3).

Regarding nanoprecipitation, changes in aqueous phase volumes are described in Table 4. When the final volume is increased, nanosuspensions which final concentrations of DXP and DSPE-PEG$_{2000}$ are decreasing were obtained.

These results show a clear effect of volume modification on the average diameter of the nanoparticles obtained. The increase of the volume of aqueous phase produces smaller nanoparticles compared to the "standard" formulation. The PdI increases slightly but remains below 0.2, meaning that the nanoparticle size distribution remains monodisperse. In terms of size and PdI, all suspensions were stable for 15 days at 4° C.

TABLE 4

Nanoprecipitation: impact of aquous phase volume modification

| Volume acetone/water (ml) | "Standard" 2.5/5 ml | 2.5/10 ml | 2.5/20 ml |
|---|---|---|---|
| Final concentration DXP/DSPE-PEG$_{2000}$ (mg/ml) | 5/2.5 | 2.5/1.25 | 1.25/0.625 |
| $d_H$ (nm) | 230 | 150 | 125 |
| PdI | 0.06 | 0.1 | 0.13 |

Poloxamer 407 Poloxamer 188 or PEG-40-Stearate Nanoparticles

The surfactant was dissolved into 200 mL of water placed in a 1 L amber pyriform flask to reach the desired concentration (1.0, 1.5 or 2.0% w/v)). At the same time, DXP was dissolved into 10 mL of acetone volumetric flask with acetone (0.025, 0.050 and 0.075% w/v). The aqueous solution was heated at 60° C., and the organic solution was injected directly into it under stirring using a syringe needle. Acetone was then evaporated under reduced pressure using a rotary evaporator. Acetone removal was checked by $^1$H NMR. To concentrate the suspension, it was placed into a 200 mL ultrafiltration cell from Millipore (France), fitted up with a 100.000 Da regenerated cellulose membrane, under nitrogen pressure until the volume was reduced to 20 mL. Finally, trehalose was optionally added to the concentrated suspension (final concentration 0.5, 1, 2.5, 3.5 and 4.5% (w/v)) as a cryoprotectant before being frozen in liquid nitrogen and freeze-dried for 48 h using a CHRIST ALPHA 1-2 LD plus (France) freeze-drier.

HA-DPPE Coated Nanoparticles of DXP

Nanoparticles from 190 to 340 nm were obtained with a polydispersity index between 0.05 and 0.4 and a negative zeta potential of −40 to −50 mV. Nanoparticles were stable for about 30 days at 4° C.

Physico-Chemical Properties
Methods
Size, PdI and Zêta Measurement

Size and zeta potential has been studied with Zetasizer Nano-ZS from Malvern Instrument (UK). Based on quasi-elastic light scattering phenomenon, the measure was performed in triplicate at an angle of 173° at 25° C. temperature. Hydrodynamic diameter ($d_H$), polydispersity index (PdI) and zeta potential were recorded on 1/10 diluted samples in milliQ water for size or in NaCl 1 mM for zeta potential.

X-Ray Diffraction

X-ray powder diffraction (XRPD) measurements were performed using a Rigaku rotating copper anode automated diffractometer operated at 50 kV and 200 mA using Cu Kα radiation. Nanoparticles suspensions were ultrafiltrated with Amicon 100 kDa, then, the concentrate was gently introduced into sealed quartz capillaries. The X-ray beam passing through the sample is diffracted and intensity of the diffracted rays is measured as a function of the theta angle, 1 to 60°.

Stewart Assay, DSPE-PEG$_{2000}$ Quantification

To determine the amount of DSPE-PEG$_{2000}$ associated on nanoparticles, phospholipids were assayed using Charles and Stewart method (J. Charles et al., Anal. Biochem., 1980, 104, 10-14). This assay is based on the capacity of phospholipids to complex with ammonium ferrothiocyanate in organic phase. Ammonium ferrothiocyanate 0.1 M was prepared mixing 27.03 g of ferric chloride hexahydrate and 30.4 g of ammonium thyocyanate in 1 L of milliQ water. This solution is stable within several months at 4° C. Calibration curve was prepared in presence of DXP at stable concentration to avoid any interactions between these two compounds. The range of the calibration curve is 0-0.1 mg/ml, the maximal absorbance was determined at 493 nm. a good linear regression was obtained $R^2=0.99479$ and $y=5.2577x+0.0037$. Each nanoparticle suspension was divided into 3 samples after Amicon 100 kDa ultrafiltration: 1) 100 µl filtrate, 2) 2 µl concentrate, 3) 20 µl total. Each tube was completed with milliQ water qsp 1 ml, 2 ml chloroform was added and finally 2 ml of ammonium ferrothiocyanate solution previously prepared. Tubes were vortexed vigorously during 1 min. They were then subjected to centrifugation at 1000 rpm (approx. 300 g) for 5 minutes to separate the aqueous and organic phases. The aqueous phase is then removed gently with a Pasteur pipette. The assay was carried out on organic phase using a UV-Visible spectrophotometer at 493 nm.

TABLE 5

Calibration curve DXP/DSPE-PEG$_{2000}$ assay

| | Sm$_1$ DSPEPEG/ water (0.1 mg/ml) (ml) | MilliQ water (qsp 1 ml) (ml) | Sm$_2$ DXP/CHCl$_3$ (0.2 mg/ml) (ml) | Ammonium ferrothio- cyanate (ml) | DSPE-PEG concentration in CHCl$_3$ (mg/ml) |
|---|---|---|---|---|---|
| 0 | 0 | 1 | 2 | 2 | 0 |
| 1 | 0.1 | 0.9 | 2 | 2 | 0.005 |
| 2 | 0.2 | 0.8 | 2 | 2 | 0.01 |
| 3 | 0.4 | 0.6 | 2 | 2 | 0.02 |
| 4 | 0.6 | 0.4 | 2 | 2 | 0.03 |
| 5 | 0.8 | 0.2 | 2 | 2 | 0.04 |
| 6 | 1 | 0 | 2 | 2 | 0.05 |

Transmission Electron Microscopy (TEM) and Cryo-TEM

A volume of 5 µl of the nanoparticles suspension was deposited for 1 minute on copper grids formwar coated. Negative staining was performed by addition of a drop of uranyl acetate at 2% w/w for 30 seconds. Excess solution was removed and grids were left to dry before observation. The observations were carried out on a JEOL microscope at an acceleration voltage of 80 kV.

A volume of 5 µl of the nanoparticles suspension was dropped on copper grid covered by carbon film and pretreated with plasma. Blot time was 4 seconds and then the preparation was plunged into liquid ethan. Grids were stored in liquid nitrogen until observation. The observations were carried out on a JEOL JEM1400 Lab6 microscope at an acceleration voltage of 12 kV. Pictures were taken with DFocus −6 µm.

HPLC Quantification of Dexamethasone Palmitate and Dexamethasone

Determination of DXP concentration in the nanoparticle suspension was performed by HPLC. A Waters 717 Plus autosampler chromatographic system was employed equipped with a Waters 1525 binary HPLC pump, a Waters 2487 dual λ absorbance detector, and a Breeze software. The analysis was performed at 240 nm using a SymmetryShield™ RP18 column (5 µm, 250×4.6 mm; Waters). Column temperature was maintained at 40° C. The mobile phase was composed by a mixture of acetonitrile and milliQ water: 85/15 v/v for DXP and 35/65 v/v for DXM. The mobile phase flow was 1.2 ml/min, injection volume was 50 µl and run time was 30 min. Retention times were 24 min and 9 min for DXP and DXM respectively. In case of quantification after extraction from plasma or organs, HPLC conditions were the same and the retention times of internal standard are 21 min for testosterone decanoate (TestD) (internal standard of DXP) and 26 min for dexamethasone acetate (DXA) (internal standart of DXM). Calibration curves in acetonitrile were linear for DXP from 0.1 to 20 µg/ml ($R^2=0.9984$, $y=51800x-629.22$) and for DXM from 0.05 to 20 µg/ml ($R^2=0.9992$, $y=71775x-5604.6$).

Results

Stability Studies: Size, PdI and Zeta Potential

Emulsification-Solvent Evaporation

The studied formulation presents final concentrations of DXP/DSPE-PEG2000: 5/2.5 mg/ml, prepared in organic phase and aqueous phase volumes of 1 ml and 10 ml respectively. The size and the polydispersity index formulations are stable at 4° C. until at least day 37 but show instability from day 14 at room temperature (FIG. 1A). Beyond two weeks of storage, there is the appearance of many populations of high particle size, so that is difficult to represent graphically. The zeta potential appears to be stable up to day 37, about −50 mV, when the suspensions are stored at 4° C. At room temperature, the zeta potential measurements were stopped after day 14 because the very large diameter of the particles formed did not allow the measurement (FIG. 1B). Nanoparticles prepared using PVA had a size comprised between 150 and 180 nm and a PdI of 0.06 and 0.0184.

Nanoprecipitation

Figure 2:
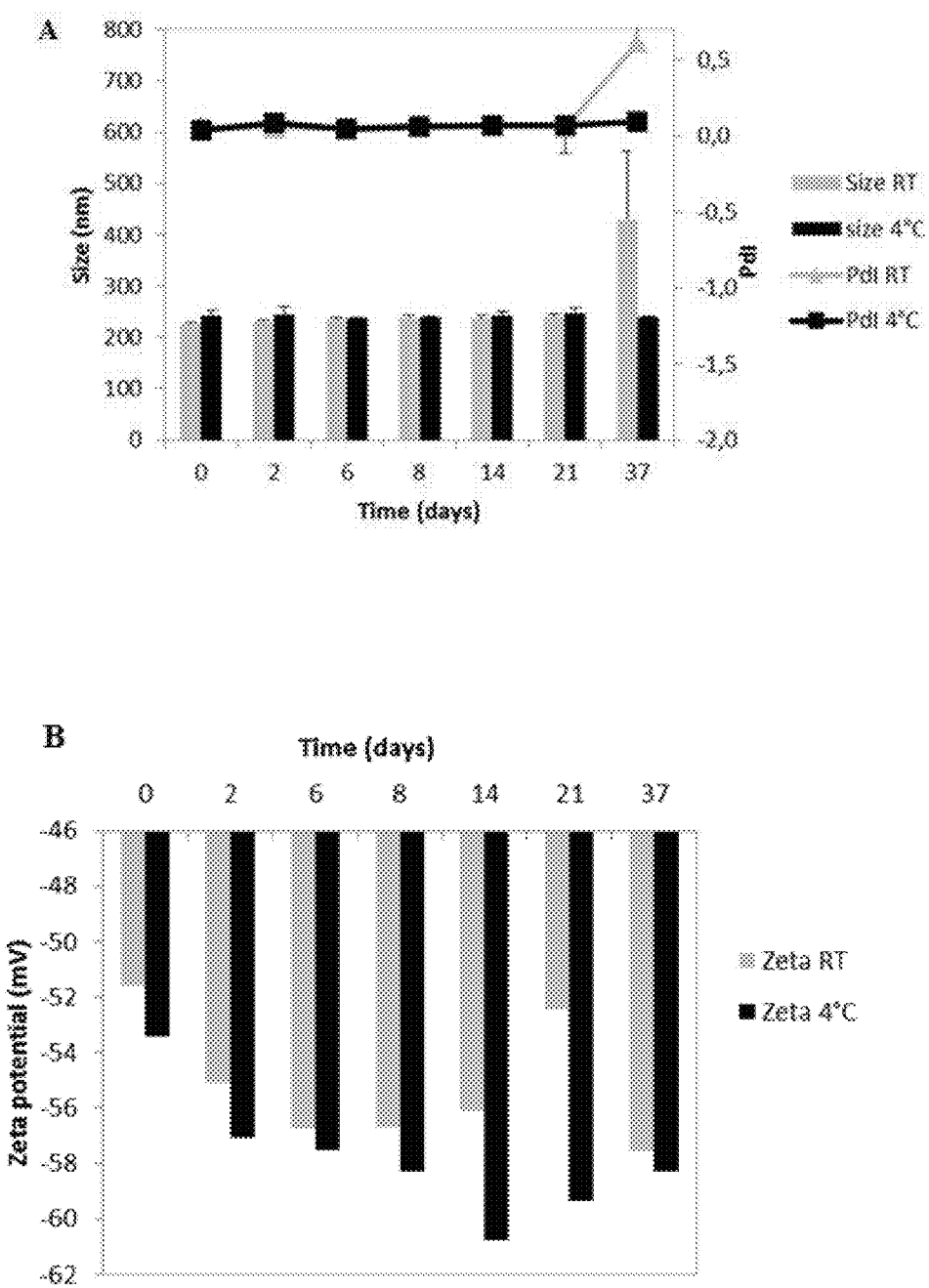
FIG. 2 is a graph showing: A: the hydrodynamic diameter overtime for nanoparticles obtained by nanoprecipitation process at room temperature, n=8 (in grey) and at T=4° C., n=5 (in black); and the polydiversity index (PdI) for nanoparticles obtained by nanoprecipitation process at room temperature, n=3 (in grey) and at T=4° C., n=4 (in black); B: Zeta potential overtime for nanoparticles obtained by nanoprecipitation process at room temperature, n=3 (in grey) and at T=4° C., n=4 (in black).

The "standard" formulation has final concentrations of DXP/DSPE-PEG$_{2000}$: 5/2.5 mg/ml, formulated in organic phase and aqueous phase volumes of 2.5 ml and 5 ml, respectively. At a temperature of 4° C., the size and PdI are stable up to 37 days after preparation. However, these particles are not stable when stored at room temperature. Under these conditions is observed a significant increase in average particle diameter (FIG. 2A). However, the zeta potential of the nanoparticles formed by nanoprecipitation is around −60 mV (FIG. 2B). It is stable until day 37, regardless of the storage temperature.

Figure 3:
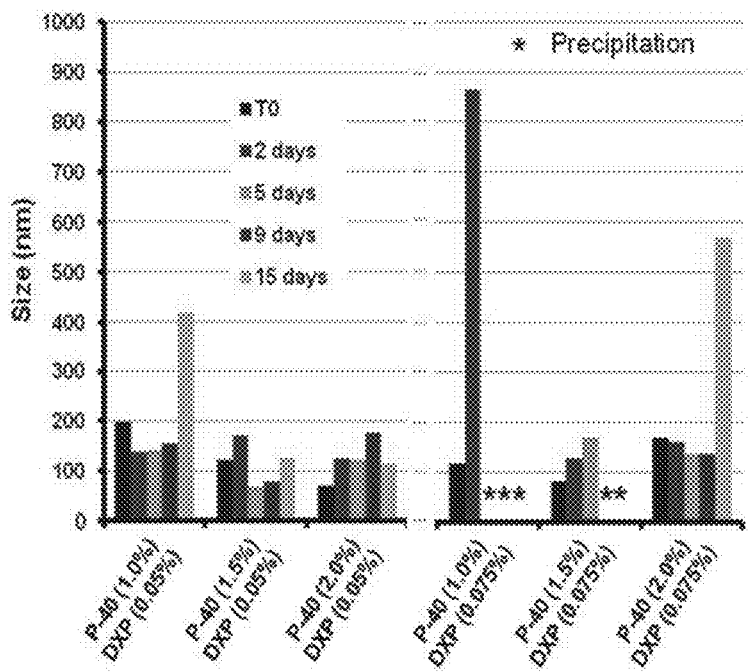
FIG. 3 is a graph showing the size of nanoparticles prepared with various amount of PEG-40-Stearate (P-40) and dexamethasone palmitate over time upon storage at room temperature.

Alternatively DXP can be formulated using PEG-40 stearate, leading to nanoparticles of about 80 to 200 nm depending of surface coating material concentration (FIG. 3). The highest PEG-40 stearate concentration (2%) lead to nanoparticles between 100 and 200 nm that are stable for up to 9 days.

Figure 4:
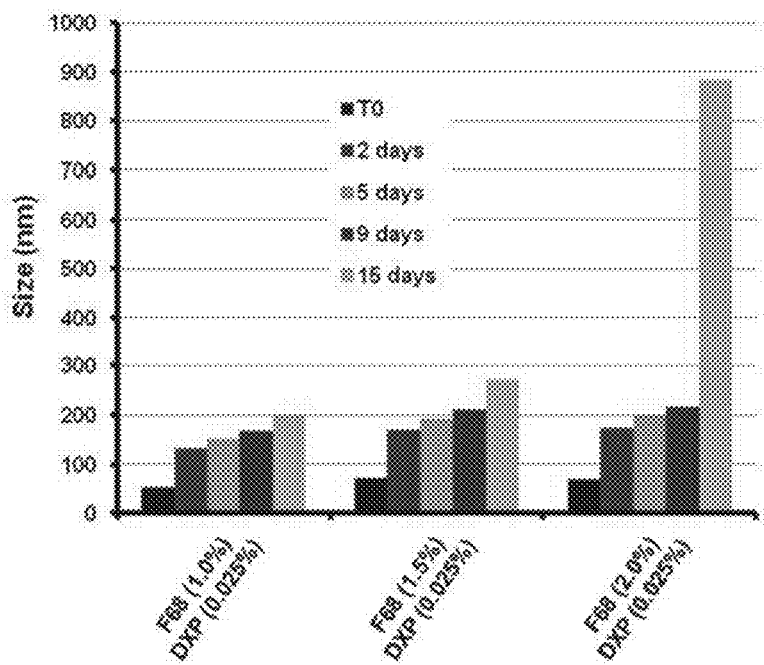
FIG. 4 is a graph showing the size of nanoparticles prepared with various amount of poloxamer 188 (F68) and dexamethasone palmitate over time upon storage at room temperature.

Alternatively DXP can be formulated using poloxamer 188 (F68) (FIG. 4). DXP nanoparticle size initially around 50 nm increased above 100 nm with PDIs between 0.03 and 0.3 within two days of preparation and kept increasing afterwards until aggregation/precipitation.

Alternatively DXP can be formulated using poloxamer 407 (F127). The formulations prepared with DXP at 0.05%

Figure 5:
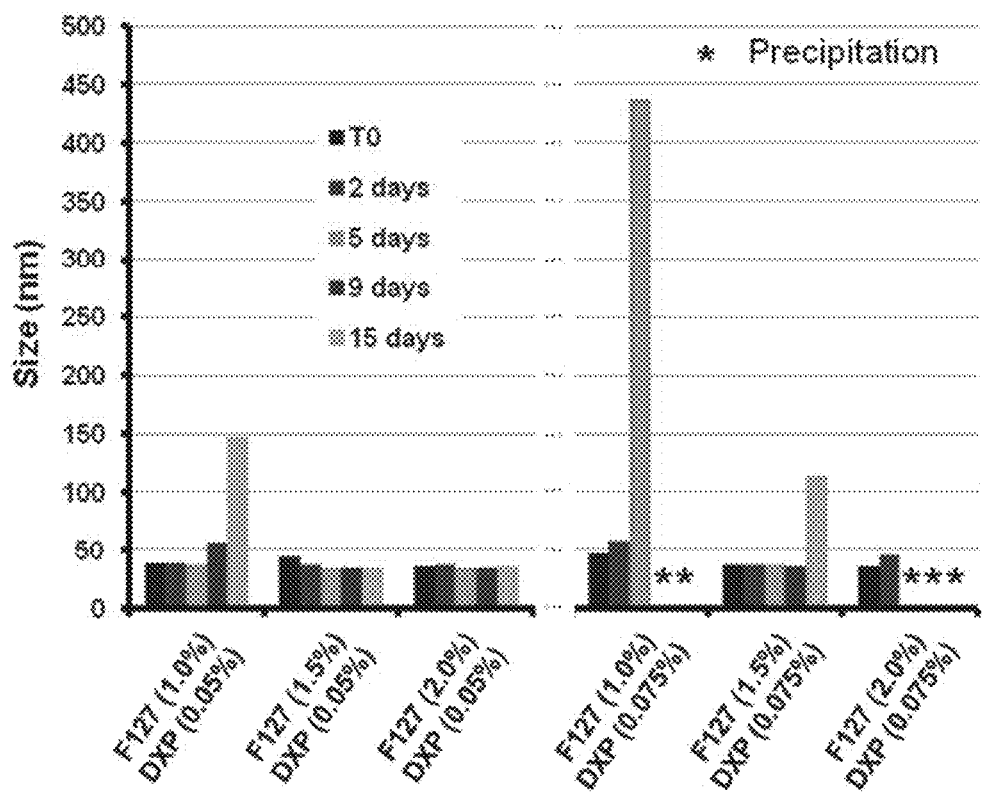
FIG. 5 is a graph showing the size of nanoparticles prepared with various amount of poloxamer 407 (F127) and dexamethasone palmitate over time upon storage at room temperature.

(w/v) and F127 concentrations 1.5 and 2.0% (w/v) remained stable for 15 days. In both cases the average size of the nanoparticles remained unchanged, around 40 nm with PdIs between 0.12 and 0.27. When DXP concentration was increased to 0.075% (w/v), the suspension prepared with F127 at 1.5% (w/v) was totally stable during at least 9 days. The average size of the particles remained around 40 nm with PdIs between 0.13 and 0.16 (FIG. 5).

Physico-Chemical Characterization

X-Ray Diffraction

In order to study the structure and internal organization of nanoparticles, we conducted analyses of different nanosuspensions by X-ray diffraction.

Five different formulations were analyzed: (1) nanoparticles formed by nanoprecipitation (referred to as Nanoprecipitation), (2) the same formulation after 6 weeks storage at room temperature (Nanoprecipitation to 6 weeks), (3) nanoparticles obtained by emulsion-evaporation (Emulsion-evaporation), (4) the same formulation after 3 weeks of conservation (Emulsion-evaporation three weeks), (5) nanoparticles formed nanoprecipitation of DXP in an aqueous solution of poloxamer 407 (Nanoparticles DXP/Poloxamer407). The spectrum of DXP crystallized in acetone was also performed (DXP crystallized acetone).

Figure 6:
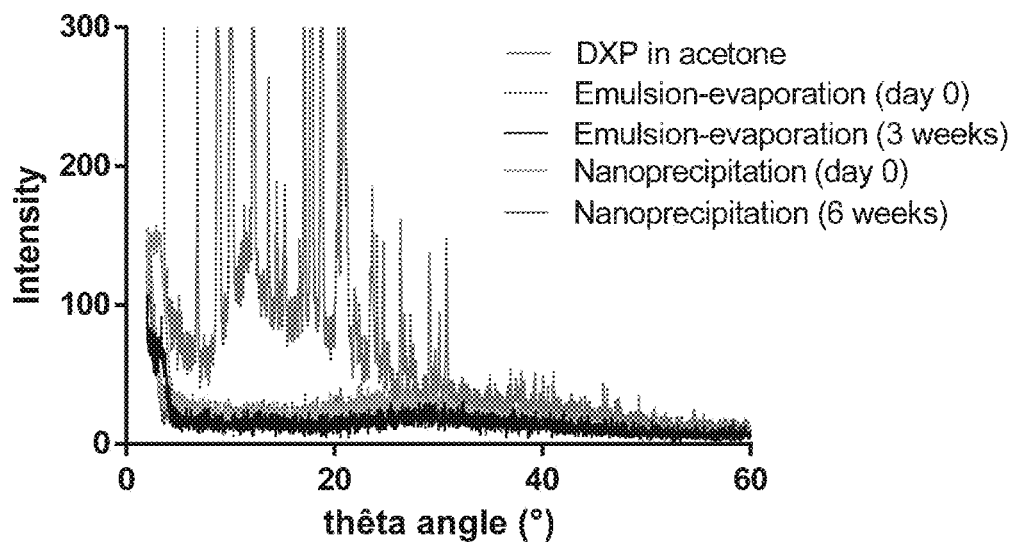
FIG. 6 is a graph showing X ray diffraction spectra of nanoparticles of the invention over time and X ray diffraction spectra of DXP crystallized in acetone.

The spectrum of DXP crystallized in acetone (FIG. 6) has many diffraction peaks that prove the DXP is in crystalline form. We clearly see the difference between the spectrum of the crystal DXP and the 5 nanoparticles formulations. The general profile of shaped curve "bump" is typical of the presence of an amorphous compound. Results clearly show this pattern in the spectrum of the five nanoparticles meaning that these formulations do not present any crystalline organization. On the contrary, this figure proves that, regardless of the process, nanoparticles are always structured as amorphous aggregates of DSPE-PEG$_{2000}$ and DXP or poloxamer 407 and DXP.

Figure 7:
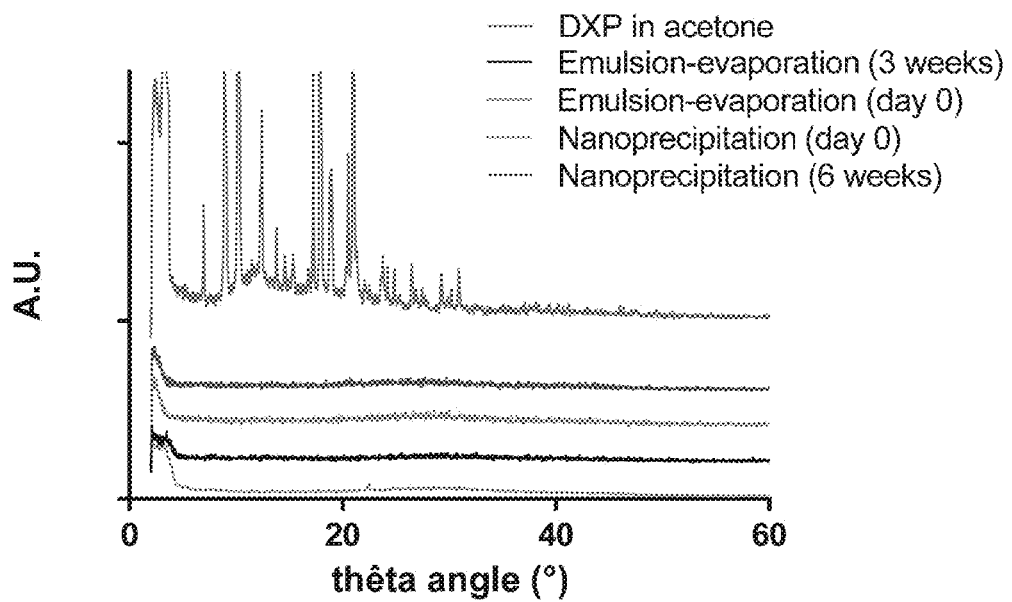
FIG. 7 is a graph showing X ray diffraction spectra of nanoparticles of the invention over time.

In FIG. 7, which shows the diffraction patterns of the five formulations investigated, separated from each other so that one can compare, is not observed clearly visible diffraction peak on the five spectrum (FIG. 7).

DSPE-PEG2000 Assay

The calibration curve of DSPE-PEG$_{2000}$ assay in presence of DXP was performed in duplicate in a range of concentrations from 0 to 0.1 mg/ml DSPE-PEG$_{2000}$ with a constant concentration ratio DXP/DSPE PEG$_{2000}$: 2/1 in order to take into account any potential interaction between DXP and DSPE-PEG$_{2000}$ in the assay. An absorption spectrum enabled to set the maximum wavelength at 493 nm.

After ultrafiltration of nanoparticle suspensions on Amicon filters (100 kDa), DSPE-PEG$_{2000}$ is determined in the concentrate, the filtrate and the total sample not ultrafiltered. Table 6 below shows the results for a formulation made by nanoprecipitation and formulation emulsion-evaporation.

Considering the accuracy of the assay, most of the DSPE-PEG$_{2000}$ is present in the concentrate for both methods of preparation. However, regarding nanoparticles formed by nanoprecipitation, DSPE-PEG$_{2000}$ concentration measured in the total does not match the total theoretical concentration. Furthermore, the concentration in the concentrate after ultrafiltration is slightly smaller than the experimental total. It can be assumed that there is a loss of some nanoparticles when ultrafiltration on Amicon.

TABLE 6

DSPE-PEG$_{2000}$ assay in nanoprecipitation and emulsification-solvent evaporation nanoparticles

| Concentration DSPE-PEG$_{2000}$ | Nanoprecipitation (mg/ml) | Emulsification-solvent evaporation (mg/ml) |
|---|---|---|
| Filtrate | 0.02 | 0.004 |
| Concentrate | 1.95 | 2.35 |
| Total | 2.14 | 2.39 |
| Theorical concentration in total nanosuspension | 2.50 | 2.50 |

Surface PEG Density—Test A

In order to calculate PEG density on the surface of nanoparticles, two hypotheses were admitted: (1) 100% of the DSPE-PEG$_{2000}$ is associated to nanoparticles, this was proved by Stewart assay previously, (2) 100% of PEG chains are on the surface of the nanoparticles, not inside the matrix. This last hypothesis seems realistic because the PEG is hydrophilic, indeed during preparation of nanoparticles DSPE-PEG$_{2000}$ in organic solution is injected into the aqueous phase, so it can be assumed that the lipophilic portion DSPE stands at the interface of nanoparticle, while the PEG is spread on the surface.

The data necessary for the calculation are as follows. The density of the DXP is $\rho_{DXP}=1.12$ g/cm$^3$, the average diameter of the nanoparticles is d=130 nm, and the molar mass of DSPE-PEG$_{2000}$ is $M_{DSPEPEG2000}=2805.54$ g/mol.

With these data, the surface area ($S_{sp}$, specific surface) of the suspension can be calculated (Equation 1).

$$S_{sp} = \frac{6}{\rho d} = \frac{6}{1.12 \times 10^6 \times 130 \times 10^{-9}} = 41.2 \text{ m}^2/\text{g}. \quad \text{Equation 1}$$

Thus, the surface available ($S_{available}$) within one nanosuspension is calculated by Equation 2.

$$S_{available} = Ssp \times (m(\text{DXP}) + m(\text{DSPEPEG2000})) = 41.2 \times 75 \times 10^{-3} = 3.09 \text{ m}^2/\text{suspension}. \quad \text{Equation 2}$$

In addition, the number of DSPE-PEG$_{2000}$ in the suspension is calculated by Equation 3.

$$N_{DSPEPEG} = \frac{m}{M} \times Na = \frac{25 \times 10^{-3} \times 6.023 \times 10^{23}}{2805.54} = 5.37 \cdot 10^{18} DSPE\text{-}PEG_{2000}/\text{suspension}. \quad \text{Equation 3}$$

Using these three values, it is possible to deduce the surface available per PEG chain on the surface of the nanoparticles (Equation 4).

$$\text{Surface}_{PEG} = \frac{Sdisp}{N(DSPEPEG)} = \frac{3.091}{5.37 \cdot 10^{18}} = 5.75 \cdot 10^{-19} \text{ m}^2/DSPE\text{-}PEG_{2000}. \quad \text{Equation 4}$$

The surface available per PEG chain on the surface of the nanoparticles formed by the solvent emulsification-solvent evaporation is therefore 0.57 nm$^2$/PEG.

The same calculation can be performed for nanoparticles formed by nanoprecipitation considering the assumptions mentioned above true. Thus, for an average diameter of 230 nm, a surface available of 0.33 nm²/PEG was obtained for nanoparticles formed by nanoprecipitation.

Transmission Electron Microscopy (TEM)

Emulsification-Solvent Evaporation

Figure 8:
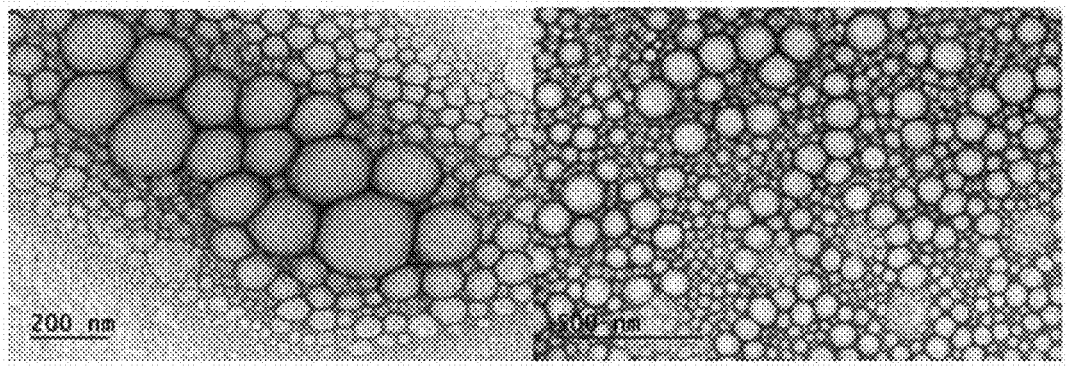
FIG. 8 is two TEM photography showing nanoparticles obtained by emulsion-evaporation.

The imaged formulation corresponds to the "standard" DXP/DSPE-PEG$_{2000}$: 5/2.5 mg/ml, formulated in organic and aqueous phases volumes of 1 ml and 10 ml respectively. According to the images observed by TEM (FIG. 8), the emulsion-evaporation process produces small spherical nanoparticles, with higher polydispersity index than nanoprecipitation. Indeed, it is observed that the mean diameter of the nanoparticles is lower than 200 nm. This result is consistent with the measurements done by dynamic light scattering described above.

Nanoprecipitation

Figure 9:
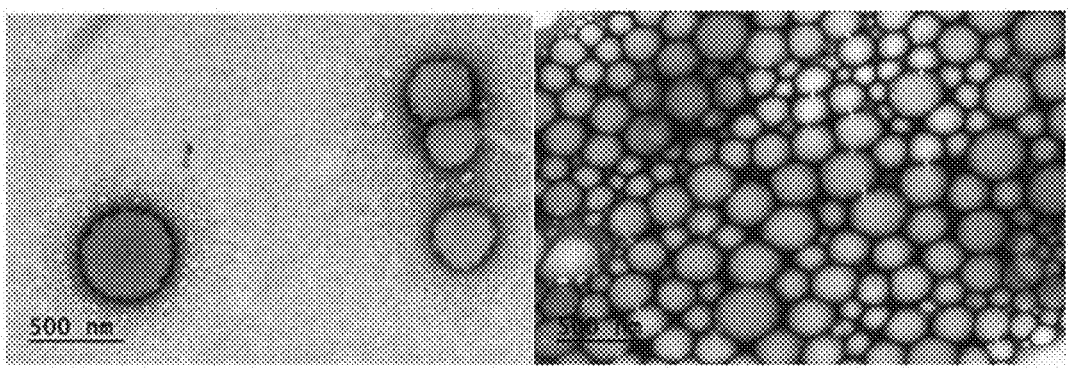
FIG. 9 is two TEM photography showing nanoparticles obtained by nanoprecipitation.

The imaged formulation corresponds to the "standard" DXP/DSPE-PEG$_{2000}$: 5/2.5 mg/ml, formulated in organic and aqueous phases volumes of 2.5 ml and 5 ml respectively. FIG. 9 clearly show that nanoparticles from the nanoprecipitation process presented characteristics correlated to DLS measurements. Indeed, the mean diameter of these nanoparticles appears to be about 200-250 nm with a monodisperse distribution. In addition, the particles are spherical.

CRYO-Transmission Electron Microscopy (CRYO-TEM)

Emulsification-Solvent Evaporation

Figure 10:
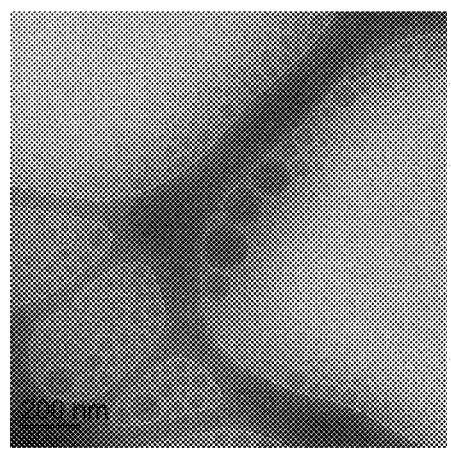
FIG. 10 is a cryo-TEM photography showing nanoparticles obtained by emulsion-solvent evaporation.

Cryo-TEM images show that "standard" emulsification-solvent evaporation nanoparticles present a clear spherical shape, with uniform matrix density within the totality of the object. Size, less than 200 nm, is consistent with DLS measurements and TEM images previously described. Cryo-TEM images present nanoparticles with large range of size, apparently from 30 to 200 nm, although DLS measurements detected a monodisperse population of particles. This range of size, still correspond to a formulation suitable for intravenous administration (FIG. 10).

Dexamethasone Loading within Nanoparticles

In order to determine DXP encapsulation inside nanoparticles, DXP assay supported by HPLC were conducted. After nanosuspension separation by ultrafiltration Amicon, the obtained filtrate and concentrate as well as the non ultrafiltrated total suspension were diluted in acetonitrile to theoretically achieve concentrations within the calibration performed previously. Table 7 presents the results for both formulations obtained either by nanoprecipitation or emulsion-solvent evaporation.

TABLE 7

DXP loading determination by HPLC

| DXP concentration (mg/ml) | Nanoprecipitation | Emulsification-solvent evaporation |
|---|---|---|
| Filtrate | 0.01 | 0.01 |
| Concentrate | 3.1 | 4.8 |
| Total (non filtrated) | 5.4 | 5.0 |
| Theoretical total concentration | 5 | 5 |
| Drug loading | 57% | 96% |

For both, a very low DXP concentration is detected in the filtrate, about 0.2% of the total, suggesting that most of the DXP is encapsulated. Concerning emulsification-solvent evaporation process, DXP concentrations in the concentrate and the total are similar and correspond to the theoretical concentration calculated from weighing during the preparation of nanoparticles. Moreover, only 0.01 mg/ml DXP were detected in the filtrate, meaning that 0.2% of the total DXP is not associated to nanoparticles. It can therefore be concluded that drug loading for this process is about 100%.

As well for nanoprecipitation, DXP concentration measured in the total suspension (non ultrafiltrated) match the calculated theoretical concentration. However, only 57% of the DXP is detected in the concentrate (3.4 mg/ml) compared to the total (5.4 mg/ml). This phenomenon has also been observed to a lesser extent in DSPE-PEG$_{2000}$ assay previously described. One hypothesis could be that a fraction of the nanoparticles were lost during the Amicon ultrafiltration process by retention thereof in the filter. However, as the concentration of DXP in the filtrate is low, this suggests that about 100% DXP is encapsulated in the nanoparticles.

In Vitro Study

In Vitro Cell Viability

Methods

During inflammatory diseases development, immune cells such as macrophages play a critical role within inflammatory pathways, cytokines production and diapedesis. The influence of the nanoparticles in the cell viability was studied in the RAW 264.7 cell line using a colorimetric method. Cells were seeded in 96-well plates at a density of 8×10³ cells/well in 100 µL of culture medium, and they were left overnight in the incubator. Afterwards, the nanoparticles at different concentrations were added to some wells, and milli-Q water diluted in medium to the control cells. Beside, nanoparticles alone in culture medium were also tested to check their interference with the absorbance. The plates were incubated for 24 hours and the yellow tetrazolium MTT (3-(4, 5-dimethylthiazolyl-2)-2,5-diphenyltetrazolium bromide) was added at a final concentration of 500 µg/mL and incubated for another hour. The MTT is reduced by metabolically active cells to form the purple formazan crystals. After the formation of the crystals, the medium was replaced by 100₄ of DMSO to dissolve them and the absorbance was measured at 570 nm. The formula used to calculate the cell viability was the following:

$$\% \text{ Cell viability} = \frac{(\text{Abs cells} + NPs) - \text{Abs}(NPs + DMEM)}{\text{Abs cells} - \text{Abs } DMEM} \times 100$$

Results

Figure 11:
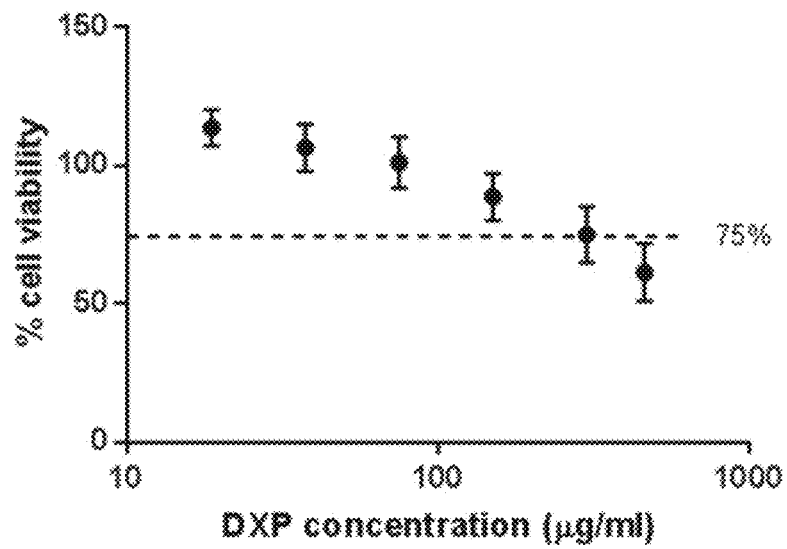
FIG. 11 is a graph showing the percentage of cell viability on macrophages in presence of an increasing amount of nanoparticles obtained by emulsification-solvent evaporation.

Usually, toxicity using this assay is determined if the cell viability goes under 75%. In this study, a range of DXP concentrations nanoparticles were tested from 18.75 µg/ml up to 460 µg/ml. FIG. 11 clearly show that nanoparticles start to present cytotoxicity activity at DXP concentration higher than 300 µg/ml. This concentration is considered to be very high and unreachable during in vivo studies and pharmaceutical applications. Indeed, in in vivo studies performed on this nanoparticles, the maximum dose injected to mice were 300 µg of DXP per mouse, that correspond logically to DXP body concentration lower than 300 µg/ml.

Same cytotoxicity experiments were performed with free dexamethasone, dexamethasone sodium phosphate, within a range of concentrations. It appears that dexamethasone alone does not have any toxicity up to 1000 µg/ml on macrophages.

Anti-Inflammatory Activity

Methods

For the cytokine release experiment, the RAW 264.7 cells were seeded in 24-well plates at a cellular density of 4×10⁴ cells/well in culture medium and they were left in the incubator for 48 hours to reach 80% confluency. Then, the medium was replaced by fresh medium alone or fresh medium with LPS at 0.1 µg/mL, and the plates were incubated another 3 hours. Afterwards, the "standard" nanoparticles produced by emulsification-solvent evaporation at three concentrations: 1, 10 and 100 µg/mL of DXP and free dexamethasone phosphate at 82 µg/ml, which correspond to 100 µg/ml DXP considering molecular weight ratio, were added to some wells. Culture medium alone was used as negative control and LPS 0.1 µg/mL as positive control.

After 24 hours of incubation with the treatments, the supernatants were collected and frozen at −20° C. until the analysis was performed. The cells were detached and counted.

The mouse inflammatory cytokines TNFα, MCP-1, IL-10 and IL-6 were quantified using a Cytometric Beads Array (CBA) detection kit (BD Biosciences, USA). This study was performed in triplicate.

Results

Figure 12:
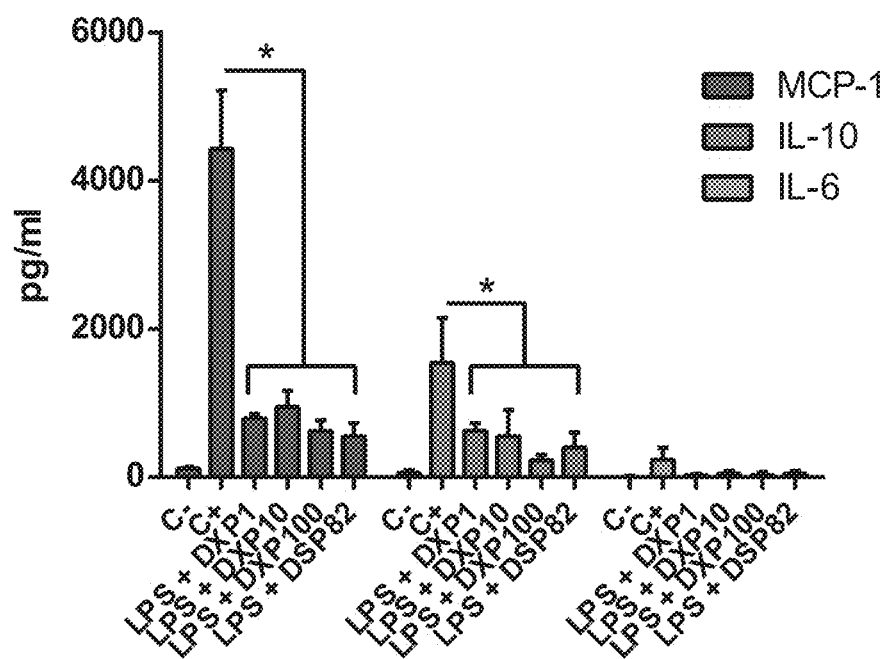
FIG. 12 is a graph showing the activity of nanoparticles obtained by emulsification-solvent evaporation on cytokines (MCP-1, IL-10 and IL-6) release from macrophages. (LPS=Lipopolysaccharide, DXP1=dexamethasone palmitate at 1 µg/ml, DXP10=dexamethasone palmitate at 10 µg/ml, DXP100=dexamethasone palmitate at 100 µg/ml, DSP82=dexamethasone phosphate at 82 µg/ml).
Figure 13:
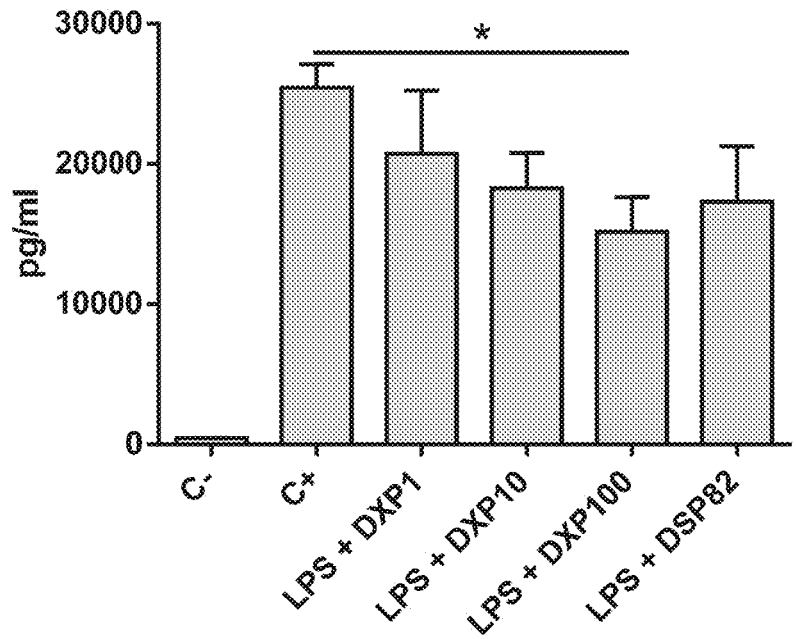
FIG. 13 is a graph showing activity of nanoparticles obtained by emulsification-solvent evaporation on TNFα release from macrophages. (LPS=Lipopolysaccharide, DXP1=dexamethasone palmitate at 1 µg/ml, DXP10=dexamethasone palmitate at 10 µg/ml, DXP100=dexamethasone palmitate at 100 µg/ml).

The release of four different pro-inflammatory cytokines (MCP-1, IL-10, IL-6, TNFα) by macrophages into the cell culture medium was quantified. Anti-inflammatory effect of the nanoparticles appears clearly on FIGS. 12 and 13. The chemokine MCP-1 were strongly and significantly reduced by DXP nanoparticles in presence of LPS. Regardless of DXP concentration in nanoparticles, no dose-effect appeared, meaning that a nanoparticles DXP concentration of 1 µg/ml is enough to get the awaited/expected anti-inflammatory effect. Moreover, nanoparticles DXP concentration of 1 µg/ml leads to the same anti-inflammatory activity than free molecule at 82 µg/ml. This clearly shows the interesting benefit of using nanoparticles instead of free drug. Then, same conclusions can be attributed to the IL-10 release. Indeed, significant reduction of IL-10 release was observed after treatment with DXP nanoparticles, regardless DXP concentrations. Concerning IL-6 release, results are more balanced. No significant reduction was detected for DXP nanoparticles and free dexamethasone, but a downward trend can be observed in details. Interestingly, DXP concentration in nanoparticles has an impact on TNFα release. Indeed, only 100 µg/ml DXP in nanoparticles were able to reduce significantly the release of this important pro-anti-inflammatory cytokine, whereas no effect detected with free dexamethasone phosphate at the same equivalent concentration.

Figure 14:
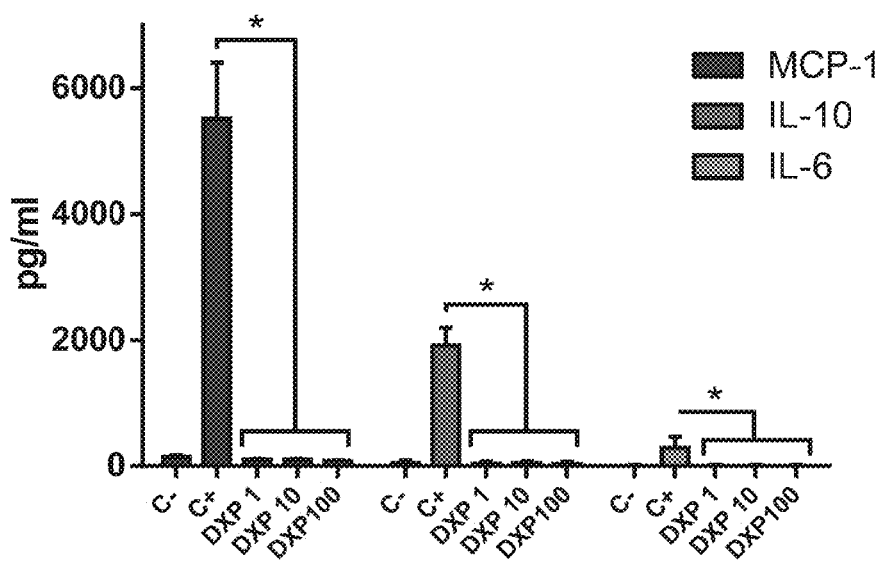
FIG. 14 is a graph showing that the nanoparticles obtained by emulsification-solvent evaporation do not induce an inflammatory activity.

Control study was performed to ensure that nanoparticles do not induce inflammatory itself. This cytokine release assay was done by treated raw264.7 cells with DXP nanoparticles or dexamethasone sodium phosphate at same concentrations as previously described but without any LPS treatment, normally used to induce inflammation. Results (FIG. 14) proves that neither DXP nanoparticles nor free drug induce pro-inflammatory cytokine release. This confirms that the developed nanoparticles are suitable for anti-inflammatory treatment as expected.

In Vivo Study
Pharmacokinetis
  Methods

Nanoparticles were prepared by emulsion-evaporation as described above and were diluted in PBS to obtain a final concentration of 2.5 mg/ml DXP, which corresponds to 1.55 mg/ml dexamethasone base. Control solution was prepared by dissolution of DSP in PBS to obtain a final concentration of 1.55 mg/ml eq. DXM. DBA/lOlaHsd male mice aged of 9 weeks (Envigo) were divided into two groups. One received the nanoparticle suspension and the other received the control, administration was carried out by intravenous injection in the tail vein at 12 mg/kg eq. DXM. For each group, 11 pharmacokinetic time points were performed with 7 mice per point, from 10 min to 48 hours. Blood sampling was achieved by terminal cardiac puncture using a 25G needle while mice were previously anesthetized with a lethal dose of pentobarbital. Immediately after, blood was centrifuged to recover plasma which was stored at −80° C. For every time point, 5 mice out of 7 underwent organs sampling after cardiac puncture. Liver, spleen, kidneys and lungs were removed and stored at −80° C.

To achieve quantification of DXM and DXP in plasma, an extraction process was developed. 100 µl of plasma samples were introduced into centrifugation tubes and 100 µl of the internal standart at 4 µg/ml in acetonitrile was added and vortexed during 30 seconds. 3 ml of a mixture chloroform/methanol: 9/1 (v/v) was added and tubes were vortexed vigorously 3 minutes. Centrifugation were performed at 3500 rpm, 30 min. Organic phase was recovered and evaporated using an evaporator under gas flow. Dried molecules were dissolved in 200 µl acetonitrile and this sample was analyzed by HPLC-UV. Calibration curves of DXP and DXM were linear, respectively in the range 0.5-100 µg/ml ($R^2=0.9997$, y=0.2199x−0.0165) and 0.1-100 µg/ml ($R^2=0.9974$, y=1.056x+0.1445). Regarding short time points (10 min, 20 min, 40 min), DXP and DXM concentrations were above the linearity range of the calibration curve. A second calibration curve for each molecule was set up, beginning with 50 µl plasma completed to 100 µl with milliQ water. Following stages were the same than previously described. Calibration curves "50 µl plasma" of DXP and DXM were linear, respectively in the range 50-800 µg/ml ($R^2=0.9808$, y=0.2229x−3.2128) and 20-400 µg/ml ($R^2=0.9986$, y=0.7178x−0.059). Internal standard was testosterone decanoate for DXP and dexamethasone acetate for DXM quantification.

Results

Figure 15:
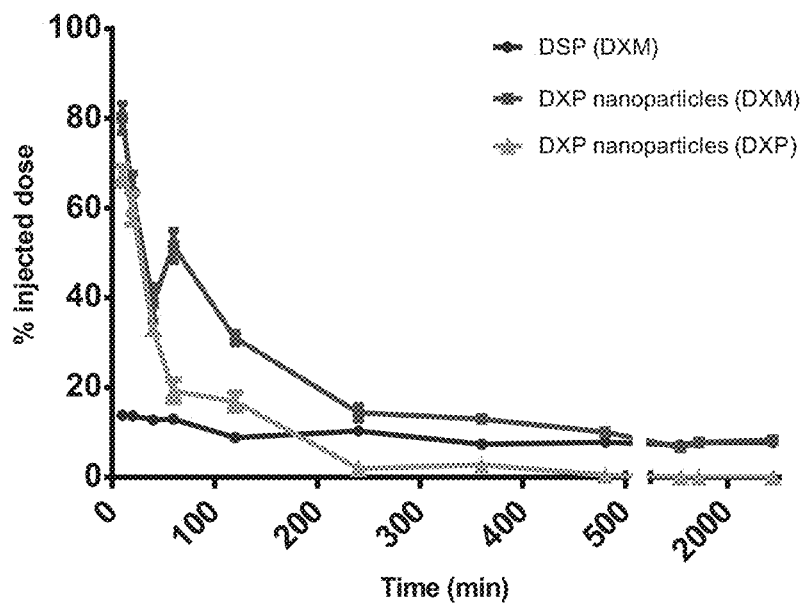
FIG. 15 is a graph showing the percentage of dexamethasone and dexamethasone palmitate in blood in function of time after intravenous injection of dexamethasone palmitate nanoparticles obtained by emulsification-solvent evaporation compared to the percentage of dexamethasone in blood in function of time after intravenous injection of dexamethasone sodium phosphate solution.

Studying pharmacokinetics of DXP nanoparticles allow to better understand the behavior of nanoparticles in vivo after IV injection. Dexamethasone palmitate is a prodrug and dexamethasone base (DXM) is the active drug released from DXP by hydrolysis. Thereby, DXM and DXP were quantified from plasma of mice injected with nanoparticles. This data could give interesting information about the release kinetic of the DXP from nanoparticles and also of DXM from DXP. DXP nanoparticles were compared to control dexamethasone sodium phosphate, water soluble molecule. Data are presented as means±error (SEM) (FIG. 15).

10 minutes after injection, DSP control solution is obviously eliminated very fast, reaching a plateau around 10% of the injected dose. DXP from nanoparticles is degraded slowly from injection until 8 h. After 8 h, no DXP was detected in mice plasma. This prodrug was transformed into DXM base, slowly released in plasma during at least 18 h. Both curves DXM, from control and nanoparticles, reached a plateau around 10% of injected dose, this plateau appears apparently because of the really high dose injected to mice, 12 mg/kg eq. DXM. There was probably an organ acting as "DXM reservoir", releasing small amounts of DXM during at least 48 h. Data were analyzed with non compartimental analysis software (Table 8).

The area under the curve ($AUC_{0 \to t}$) of DXM from nanoparticles was 31064 µg*min/ml, whereas DXM from control was 18755 µg*min/ml. After DXP nanoparticles injection, the active molecule exposure in the body is 1.6 times higher than for an aqueous injection of free molecule. Then, comparing the data up to 6 h, the $AUC_{(0 \to 240)}$ is 3.2 fold higher for DXM from nanoparticles. At $T_{max}$, 10 min for both, $C_{max}$ of DXM from nanoparticles, 128.5 µg/ml is clearly higher than the control $C_{max}$=22.1 µg/ml. Volumes of distribution (Vd) reveal that the nanoparticles are less distributed in the organs and stay longer in the blood with Vd for DXM from nanoparticles 1.8 fold lower than the control. Moreover, clearance rate is also slightly in favor of a slower elimination of the nanoparticles. However, elimination half-life is higher for the control DSP. All of these parameters triggered to the conclusion that nanoparticles show a longer retention time in the blood after IV injection compared to the free drug. Nevertheless DXP act as a prodrug, and seems to be rapidly hydrolysed to release free DXM in the blood. Even so, DXP nanoparticles play the role of "reservoir" after injection, delaying the biodistribution and metabolisation of the drug, as shown with DSP pharmacokinetic.

TABLE 8

Comparative data

|  | DSP (DXM) | Nanoparticles (DXM) |
|---|---|---|
| $t_{1/2}$ (min) | 1728 | 1236 |
| $T_{max}$ (min) | 10 | 10 |
| $C_{max}$ (µg/ml) | 22.1 | 128.5 |
| $C_0$ (µg/ml) | 22.4 | 162.8 |
| $AUC_{0 \to t}$ (µg*min/ml) | 18755 | 31064 |
| MRT (min) | 2700 | 1605 |
| Clearance (ml/min) | 0.0046 | 0.0043 |
| Vd (ml) | 12.50 | 6.93 |

Biodistribution

Figure 16:
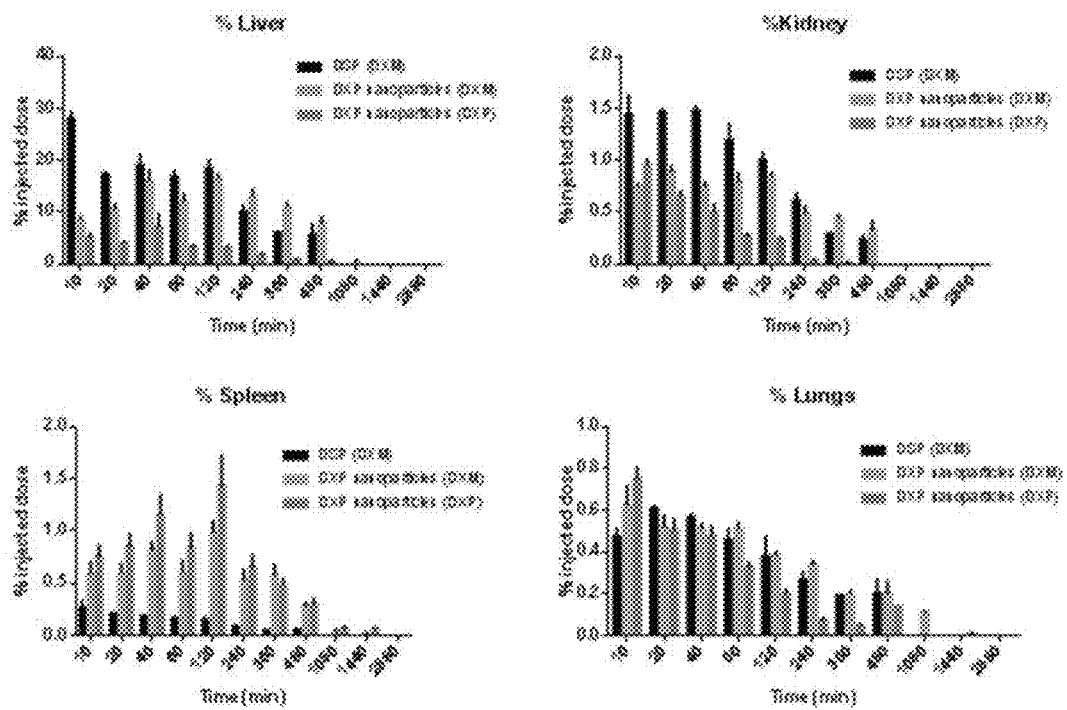
FIG. 16 are four graphs showing the biodistribution of dexamethasone and dexamethasone palmitate in liver, kidney, spleen and lungs in function of time after intravenous injection of dexamethasone palmitate nanoparticles obtained by emulsification-solvent evaporation compared to the percentage of dexamethasone in blood in function of time after intravenous injection of dexamethasone sodium phosphate solution, both injected at 12 mg/kg eq. dexamethasone.

FIG. 16 represents the biodistribution of the nanoparticles in the DXP prodrug form or in the DXM drug form, and the DSP control, both injected intravenously at 12 mg/kg eq. DXM. Liver, spleen, kidneys and lungs distribution were evaluated. Among the four, the liver presents the highest accumulation of nanoparticles, around 20% of the injected dose. However, DXP and DXM concentrations from nanoparticles in the liver are clearly lower than the control DSP. This results indicates that the PEGylation of the nanoparticles allow the carrier to escape from the immune system in the blood stream and to reduce the opsonisation of the particles. The presence of DXP and DXM in the liver is linked to the hepatic metabolisation way of the DXM. In another hand, DXP and DXM concentrations from the nanoparticles are significantly raised compared to DSP. Even though DXP in spleen represent less than 2% of the injected dose, this highest presence in this organ could be explain by the presence of the PEG at the surface of the nanoparticles, as it was described previously (M. T. Peracchia et al., J. Control. Release, 1999, 60(1), 121-128). Less than 2% of the injected dose is detected in kidneys for the 3 curves. This presence is linked to the elimination rate of the molecules. Very few quantities, less than 1%, were detected in the lungs.

Therapeutic Efficacy

Methods

Collagen-induced arthritis (CIA) model were induced to males DBA/1 mice divided into 5 groups of 10 mice each, aged of 9-11 weeks (Envigo, France) as described in the CIA Nature Protocol (D. D. Brand et al, Nat. Protoc., 2007, 2(5), 1269-1275). Mice were injected intradermally at the base of the tail, with 50 µl immunization grade chicken type II collagen (ref 20011, AMSBio, France) emulsified in complete Freund's adjuvant (ref 7001, AMSBio, France). Injections were performed at day 0 and day 21. From day 21, arthritis symptoms on forepaws and hindpaws (swelling, redness and ankylosis) were monitored every day following an inflammation scoring scale. The volume of hindpaws was also measured using a plethysmometer, giving an objective measure compared to the scoring method that can be person-dependant. The incidence of CIA model was >80%. At day 31, mice were divided into 5 groups (n=8) with a consistent score average for each group. Mice were injected intravenously at different time points. The control group PBS was injected 3 times at days 32, 34 and 36 to allow the comparison with the treatment groups. Two groups of dexamathesone sodium phosphate (DSP) were tested, with 3 injections (days 32, 34 and 36) at 0.1 mg/kg and 1 mg/kg eq. DXM. The nanoparticles DXP groups underwent the same conditions as DSP groups.

Two-way ANOVA with a post test of Newman-Keuls were performed to analyze the arthritis score graph. The nonparametric Mann-Whitney U test was applied to analyze differences between controls and individual treatments using GraphPad Prism 6.0 software. Data are expressed as mean±standard error of mean (SEM), p-values less than 0.05 were considered as statistically significant.

Results

Figure 17:
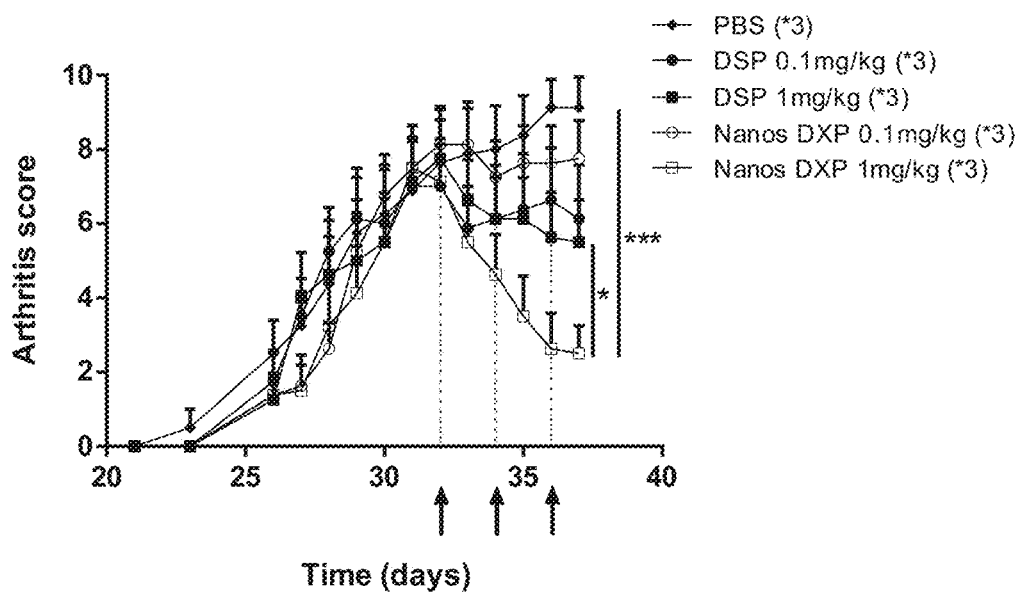
FIG. 17 is a graph showing the arthritis score of phosphate buffered saline (PBS), dexamethasone sodium phosphate solution and the dexamethasone palmitate nanoparticles represented as total arthritis score per mice (mean+/−SEM, n=5) as a function of time.

FIG. 17 shows the anti-inflammatory activity of the DXP nanoparticles represented as total arthritis score per mice (mean+/−SEM, n=5) as a function of time. These results clearly demonstrate the superiority of the DXP nanoparticles at 1 mg/kg eq.DXM, 3 injections, compared to the free drug. The statistical analysis of the curves show that a significant difference between DXP nanoparticles (1 mg/kg, 3 injections) and DSP (1 mg/kg, 3 injections) and also with the control group.

Figure 18:
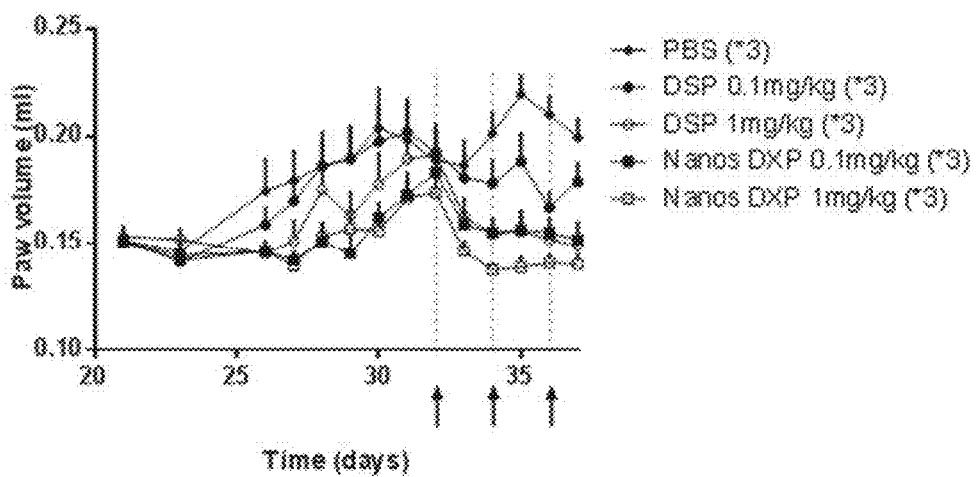
FIG. 18 is a graph showing the hindpaws volume for PBS, DSP, and nanoparticle of DXP over time.
Figure 19:
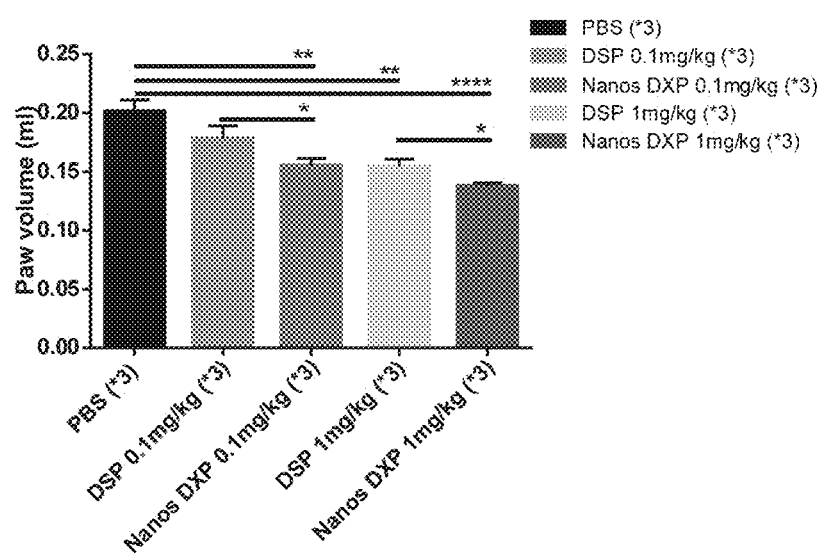
FIG. 19 is a graph showing the hindpaws volume at day 34 for PBS, DSP, Nanoparticle of DXP.

FIG. 18 shows that the decrease of the paw volume is faster than arthritis score. This explain the fact that a significant difference between DXP nanoparticles and DSP, for both dose, is observed at day 34 (FIG. 19), i.e. after only 2 injections of the treatments. Both curves are significantly different from the PBS group on days 34. Repeated administrations of DXP nanoparticles, triggered to a significant reduction of the paw volume compared to DSP solution group and to PBS control group. The DXP nanoparticles therapy allowed the mice inflammation level to fall down to complete regression of swelling and ankylosis throughout the duration of treatment.

The invention claimed is:

1. A nanoparticle comprising a glucocorticoid prodrug and a surface coating material wherein the nanoparticle size is ranging from 20 to 400 nm; wherein the surface coating material is selected from (PEG)-modified phospholipids, wherein the glucocorticoid prodrug is a lipophilic long-chain ester of a glucocorticoid; wherein the glucocorticoid prodrug is in an amorphous state; wherein the glucocorticoid prodrug loading rate is higher than 25% in weight to the weight of nanoparticle;

wherein the nanoparticle is not porous; and wherein the nanoparticle has a polyoxyethylene surface density Surface$_{PEG}$ smaller than 0.30 nm$^2$ per polyoxyethylene chain wherein $$\text{Surface}_{PEG} = \frac{S \text{ available}}{N(cot.mater.)}$$

N(cot.mater.) being the number of surface coating material molecules in the nanoparticle $$N_{(cot.mater.)} = \frac{m(cot.mater.)}{M(cot.mater.)} \times Na$$

Savailable being the surface available within the nanoparticle, $$S_{available} = Ssp \times (m(\text{prodrug}) + m(cot.mater.))$$

Ssp being the specific surface of the nanoparticle $$S_{sp} = \frac{6}{\rho d}$$

m(cot.mater.) being the mass of the surface coating material in the nanoparticle, M(cot.mater.) being the molar mass of the surface coating material, Na being the Avogadro constant, m(prodrug) being the mass of the prodrug in the nanoparticle, ρ being the density of the prodrug, and d being the average diameter of the nanoparticle.

2. The nanoparticle according to claim 1, wherein the glucocorticoid prodrug is a lipophilic long-chain ester of dexamethasone.

3. The nanoparticle according claim 1, wherein the glucocorticoid prodrug is dexamethasone palmitate.

4. The nanoparticle according to claim 1, wherein the surface coating material is 1,2-distearoyl-sn-glycero-3-phosphoethanolamine-N-[amino(polyethylene glycol)-2000] (ammonium salt).

5. A medicament comprising at least one nanoparticle according to claim 1.

6. A pharmaceutical composition comprising at least one nanoparticle according to claim 1 and at least one pharmaceutically acceptable excipient.

7. The pharmaceutical composition according to claim 6, wherein the pharmaceutical composition is formulated for intravenous administration.

8. A kit comprising a container containing a pharmaceutical composition according to claim 6.

9. A process for manufacturing at least one nanoparticle according to claim 1, including the following steps:
  performing a nanoprecipitation process or an emulsion-evaporation process starting from a solution of glucocorticoid prodrug and surface coating material in a volatile solvent and aqueous solution, or from a solution of glucocorticoid prodrug in a volatile solvent and an aqueous solution of surface coating material, and
  obtaining at least one nanoparticle comprising the glucocorticoid prodrug and the surface coating material.

10. The process of claim 9, wherein the process starts from a solution of glucocorticoid prodrug and surface coating material in volatile solvent and water.

11. The process of claim 9, wherein the process starts from a solution of glucocorticoid prodrug in volatile solvent and a water solution of surface coating material.

12. The nanoparticle according claim 2, wherein the glucocorticoid prodrug is dexamethasone palmitate.

13. The nanoparticle according to claim 2, wherein the surface coating material is 1,2-distearoyl-sn-glycero-3-phosphoethanolamine-N-[amino(polyethylene glycol)-2000] (ammonium salt).

14. The nanoparticle according to claim 3, wherein the surface coating material is 1,2-distearoyl-sn-glycero-3-phosphoethanolamine-N-[amino(polyethylene glycol)-2000] (ammonium salt).

* * * * *